United States Patent
Myers et al.

(10) Patent No.: US 11,566,291 B2
(45) Date of Patent: *Jan. 31, 2023

(54) DIFFERENTIAL METHYLATION LEVEL OF CPG LOCI THAT ARE DETERMINATIVE OF A BIOCHEMICAL REOCCURRENCE OF PROSTATE CANCER

(71) Applicants: HudsonAlpha Institute for Biotechnology, Huntsville, AL (US); THE BOARD OF TRUSTEES OF THE LELAND STANFORD JUNIOR UNIVERSITY, Palo Alto, CA (US)

(72) Inventors: Richard M. Myers, Huntsville, AL (US); James D. Brooks, Stanford, CA (US); Marie K. Kirby, Huntsville, AL (US)

(73) Assignees: HUDSONALPHA INSTITUTE FOR BIOTECHNOLOGY, Huntsville, AL (US); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 556 days.

This patent is subject to a terminal disclaimer.

(21) Appl. No.: 14/774,227

(22) PCT Filed: Mar. 13, 2014

(86) PCT No.: PCT/US2014/025848
§ 371 (c)(1),
(2) Date: Sep. 10, 2015

(87) PCT Pub. No.: WO2014/160114
PCT Pub. Date: Oct. 2, 2014

(65) Prior Publication Data
US 2016/0017435 A1 Jan. 21, 2016

Related U.S. Application Data

(63) Continuation of application No. 13/829,253, filed on Mar. 14, 2013, now abandoned.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

2013/0022974 A1\* 1/2013 Chinnaiyan .......... C12Q 1/6886
435/6.11

OTHER PUBLICATIONS

Handbook of Chemistry and Physics, 49th Edition, 1968, Weast (ed.), The Chemical Rubber Co., Cleveland, Ohio, p. A-245.\*
Strausberg et al, in Microarrays and Cancer Research, 2002, Warrington et al. (eds.), Eaton Publishing, Westborough, MA, pp. xi-xvi.\*
Notterman et al, in Microarrays and Cancer Research, 2002, Warrington et al. (eds.), Eaton Publishing, Westborough, MA, pp. 81-111.\*
Kwabi-Addo et al (Cancer Research. Proceedings: AACR 103rd Annual Meeting. Apr. 2012. 72(8 Suppl). Abstract 4999 (Year: 2012).\*

\* cited by examiner

*Primary Examiner* — Juliet C Switzer
(74) *Attorney, Agent, or Firm* — Bradley Arant Boult Cummings LLP

(57) ABSTRACT

The present disclosure provides for and relates to the identification of novel biomarkers for diagnosis and prognosis of prostate cancer or the biochemical reoccurrence of prostate cancer. The biomarkers of the invention show altered methylation levels of certain CpG loci relative to normal prostate tissue, as set forth.

4 Claims, 19 Drawing Sheets
Specification includes a Sequence Listing.

DIFFERENTIAL METHYLATION LEVEL OF CPG LOCI THAT ARE DETERMINATIVE OF A BIOCHEMICAL REOCCURRENCE OF PROSTATE CANCER

STATEMENT OF GOVERNMENT INTEREST

This invention was made with government support under Department of Defense Telemedicine and Advanced Technology Research Center (TATRC) grant number W81XWH-10-1-0790. The government has certain rights in the invention.

CROSS REFERENCE TO RELATED APPLICATIONS

This application claims the benefit of, and priority to, U.S. patent application Ser. No. 13/829,253, filed Mar. 14, 2013 titled "Differential Methylation Level of CpG Loci That are Determinative of a Biochemical Reoccurrence of Prostate Cancer

FIELD OF THE DISCLOSURE

The present invention relates to compositions and methods for cancer diagnosis, research and therapy, including but not limited to, cancer bio markers. In particular, the present invention relates to methylation levels of certain CpG loci as prognostic and diagnostic markers for prostate cancer or a biochemical recurrence of prostate cancer.

BACKGROUND

Prostate cancer is the most commonly diagnosed malignancy for men in the United States with an estimated 238,590 new cases projected for 2013. The most current means for detecting prostate cancer is a combination of a digital rectal exam (DRE) and monitoring levels of prostate-specific antigen (PSA) in the blood. Prostate-specific antigen is a protease produced by the prostate gland. PSA is present at low concentration in the blood of healthy males, and an increase in the concentration of PSA in the blood can be indicative of a prostate tumor. Until recently, PSA testing was recommended as a screening tool for all men over 50. However, two large-scale, randomized trials of PSA screening suggest that prostate cancer is over-diagnosed and over-treated, likely because many cancers that are detected are never destined to progress. Prostate cancer can have an aggressive and lethal course and an estimated 29,720 men are projected to die of prostate cancer in 2013, however, for most patients, prostate cancer is a slow growing disease. This broad range of clinical behavior is likely a reflection of the underlying genomic diversity of the tumors. Previous studies of prostate tumors reported significant heterogeneity in the gene expression profiles and genomic structural alterations including DNA copy number changes and gene fusions often involving the ETS family of transcription factors detectable in approximately half of prostate tumors. Exon sequencing of known oncogenes and tumor suppressors has found few somatic mutations and the calculated background mutation rate appears to be relatively low. This suggests the presence of other forms of genomic aberrations that contribute to the observed gene expression variations, and in turn, the diversity in tumor behavior.

Methods of detecting and/or diagnosing prostate cancer have been described previously. See for instance the following issued U.S. Pat. No. 7,524,633—Method of detection of prostate cancer; U.S. Pat. No. 7,427,476—PITX2 polynucleotide, polypeptide and methods of use therefore; U.S. Pat. No. 7,381,808—Method and nucleic acids for the differentiation of prostate tumors; U.S. Pat. No. 7,252,935—Method of detection of prostate cancer; U.S. Pat. No. 7,195,870—Diagnosis of diseases associated with gene regulation; U.S. Pat. No. 7,049,062—Assay for methylation in the GST-Pi gene; U.S. Pat. No. 6,864,093—Method of identifying and treating invasive carcinomas; U.S. Pat. No. 6,815,166—HIN-1, a tumor suppressor gene; U.S. Pat. No. 6,783,933—CACNA1G polynucleotide, polypeptide and methods of use therefore; U.S. Pat. No. 6,569,684—Method of identifying and treating invasive carcinomas; U.S. Pat. No. 5,552,277—Genetic diagnosis of prostate cancer; and U.S. Pat. No. 5,846,712 Tumor suppressor gene, HIC-1. In addition, conventional methods utilize the prostate specific antigen (PSA) blood test, and the digital rectal exam (DRE). PSA is an enzyme produced in the prostate that is found in the seminal fluid and the bloodstream. An elevated PSA level in the bloodstream does not necessarily indicate prostate cancer, since PSA can also be raised by infection or other prostate conditions such as benign prostatic hyperplasia (BPH). Many men with an elevated PSA do not have prostate cancer. Nonetheless, a PSA level greater than 4.0 nanograms per milliliter of serum was established initially as the cutoff where the sensitivity for detecting prostate cancer was the highest and the specificity for detecting non-cancerous conditions was the lowest. A PSA level above 4.0 ng per milliliter of serum may trigger a prostate biopsy to search for cancer. The digital rectal exam is usually performed along with the PSA test, to check for physical abnormalities that can result from tumor growth.

The PSA test is an imperfect screening tool. A man can have prostate cancer and still have a PSA level in the "normal" range. Approximately 25% of men who are diagnosed with prostate cancer have a PSA level below 4.0. In addition, only 25% of men with a PSA level of 4-10 are found to have prostate cancer. With a PSA level exceeding 10, this rate jumps to approximately 65%.

Current diagnostic tools for prostate cancer lack the sensitivity and specificity required for the detection of very early prostate lesions and diagnosis ultimately relies on an invasive biopsy. Once prostate cancer is diagnosed, there are no available prognostic markers for prostate cancer that provide information on how aggressively the tumor will grow. Therefore, more intrusive therapeutic routes are often chosen that result in a drastic reduction in the quality of life for the patient, even though the majority of prostate tumors are slow growing and non-aggressive. This ultimately leads to undue burden on the healthcare system and an unnecessary decrease in quality of life for the patient. The present invention addresses the need for distinguishing aggressive prostate tumors through identification of specific genomic DNA methylation biomarkers that can distinguish patients that will undergo biochemical recurrence.

DNA methyltransferases (also referred to as DNA methylases) transfer methyl groups from the universal methyl donor S-adenosyl methionine to specific sites on a DNA molecule. Several biological functions have been attributed to the methylated bases in DNA, such as the protection of the DNA from digestion by restriction enzymes in prokaryotic cells. In eukaryotic cells, DNA methylation is an epigenetic method of altering DNA that influences gene expression, for example during embryogenesis and cellular differentiation. The most common type of DNA methylation in eukaryotic cells is the methylation of cytosine residues that are 5' neighbors of guanine ("CG" dinucleotides, also referred as "CpGs"). DNA methylation regulates biological processes without altering genomic sequence. DNA methylation regulates gene expression, DNA-protein interactions, cellular differentiation, suppresses transposable elements, and X Chromosome inactivation.

Improper methylation of DNA is believed to be the cause of some diseases such as Beckwith-Wiedemann syndrome and Prader-Willi syndrome. It has also been purposed that improper methylation is a contributing factor in many cancers. For example, de novo methylation of the Rb gene has been demonstrated in retinoblastomas. In addition, expression of tumor suppressor genes have been shown to be abolished by de novo DNA methylation of a normally unmethylated 5' CpG island. Many additional effects of methylation are discussed in detail in published International Patent Publication No. WO 00/051639.

Methylation of cytosines at their carbon-5 position plays an important role both during development and in tumorigenesis. Recent work has shown that the gene silencing effect of methylated regions is accomplished through the interaction of methylcytosine binding proteins with other structural components of chromatin, which, in turn, makes the DNA inaccessible to transcription factors through histone deacetylation and chromatin structure changes. The methylation occurs almost exclusively in CpG dinucleotides. While the bulk of human genomic DNA is depleted in CpG sites, there are CpG-rich stretches, so-called CpG islands, which are located in promoter regions of more than 70% of all known human genes. In normal cells, CpG islands are unmethylated, reflecting a transcriptionally active state of the respective gene. Epigenetic silencing of tumor suppressor genes by hypermethylation of CpG islands is a very early and stable characteristic of tumorigenesis. Hypermethylation of CpG islands located in the promoter regions of tumor suppressor genes are now firmly established as the most frequent mechanisms for gene inactivation in cancers.

SUMMARY

Figure 1A:
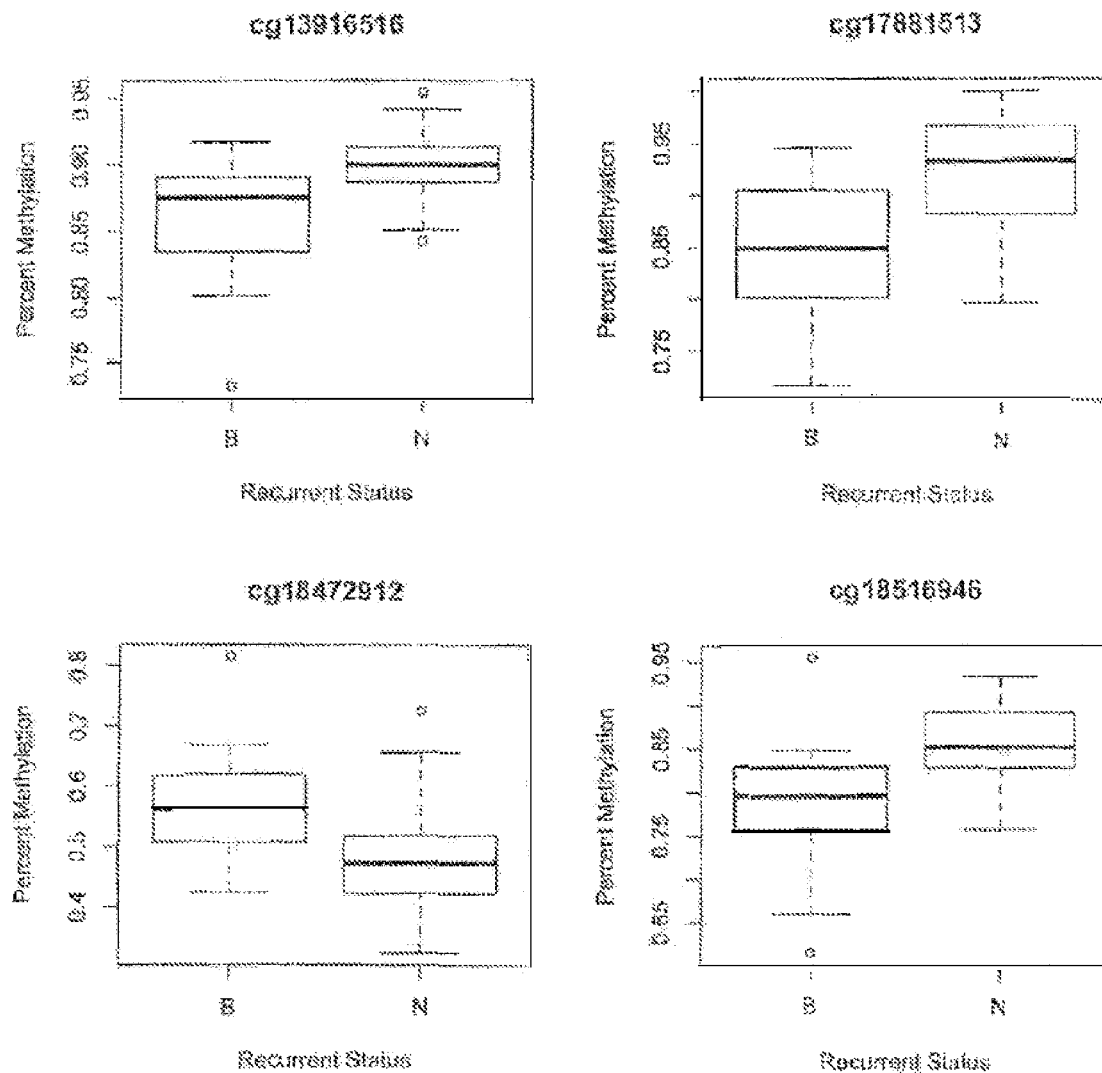
FIGS. 1A, 1B and 1C show bar graphs of the percent methylation of each of the predictive CpG loci in the biochemically recurrent patients and the non-recurrent patients. B=biochemically recurrent patients, N=patients that are not biochemically recurrent.
Figure 1A:
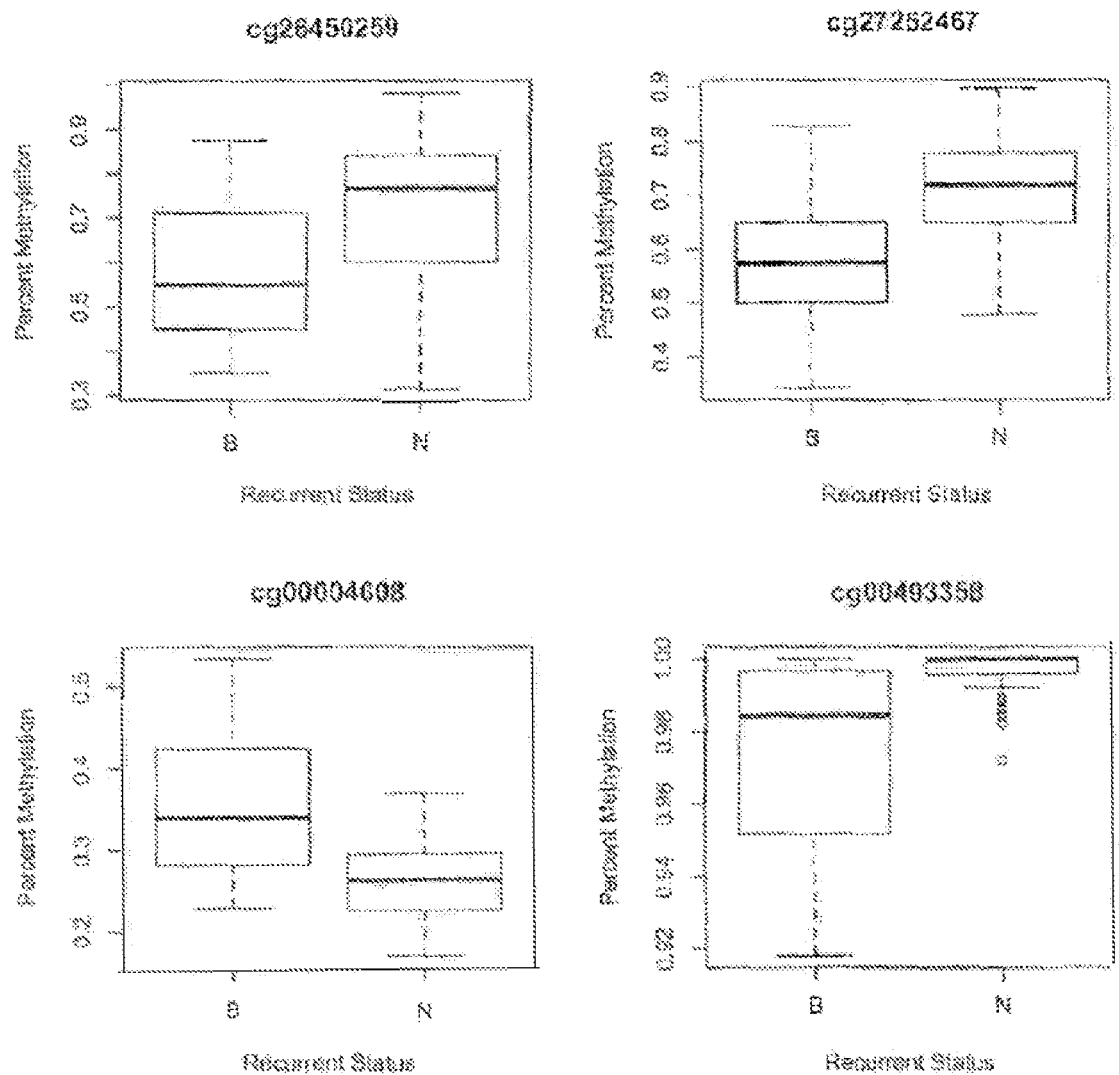
Figure 1A:
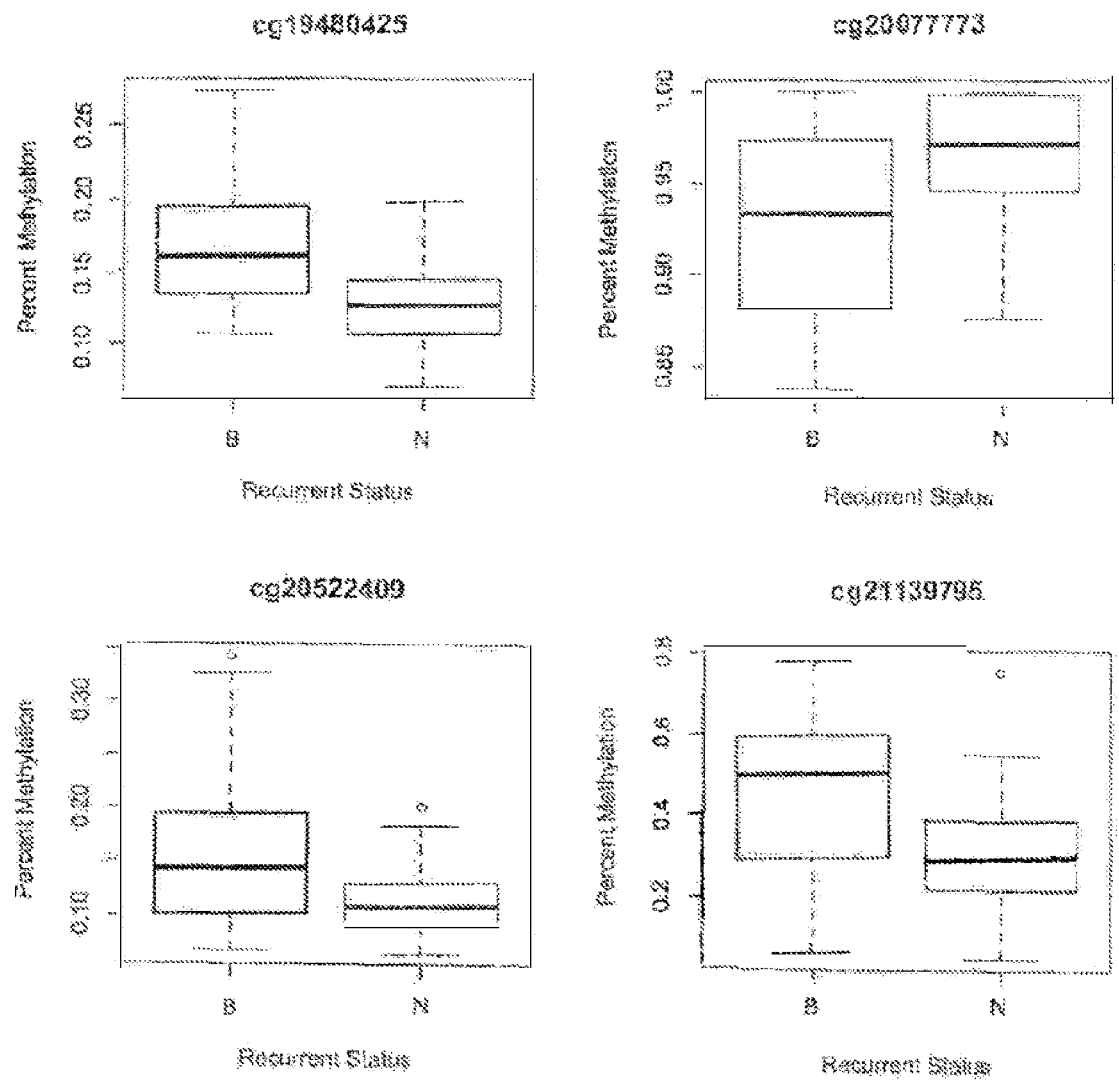
Figure 1A:
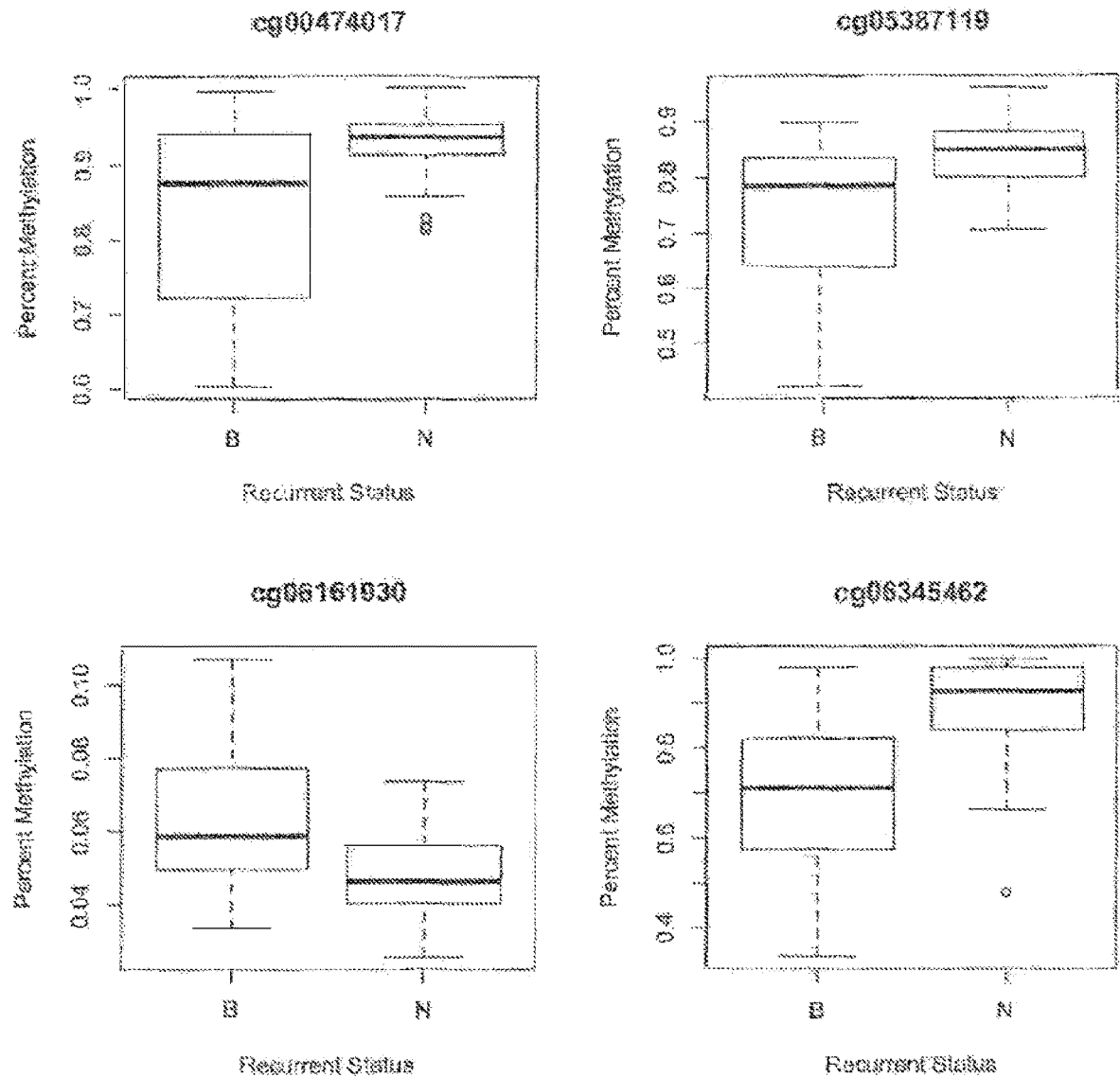
Figure 1A:
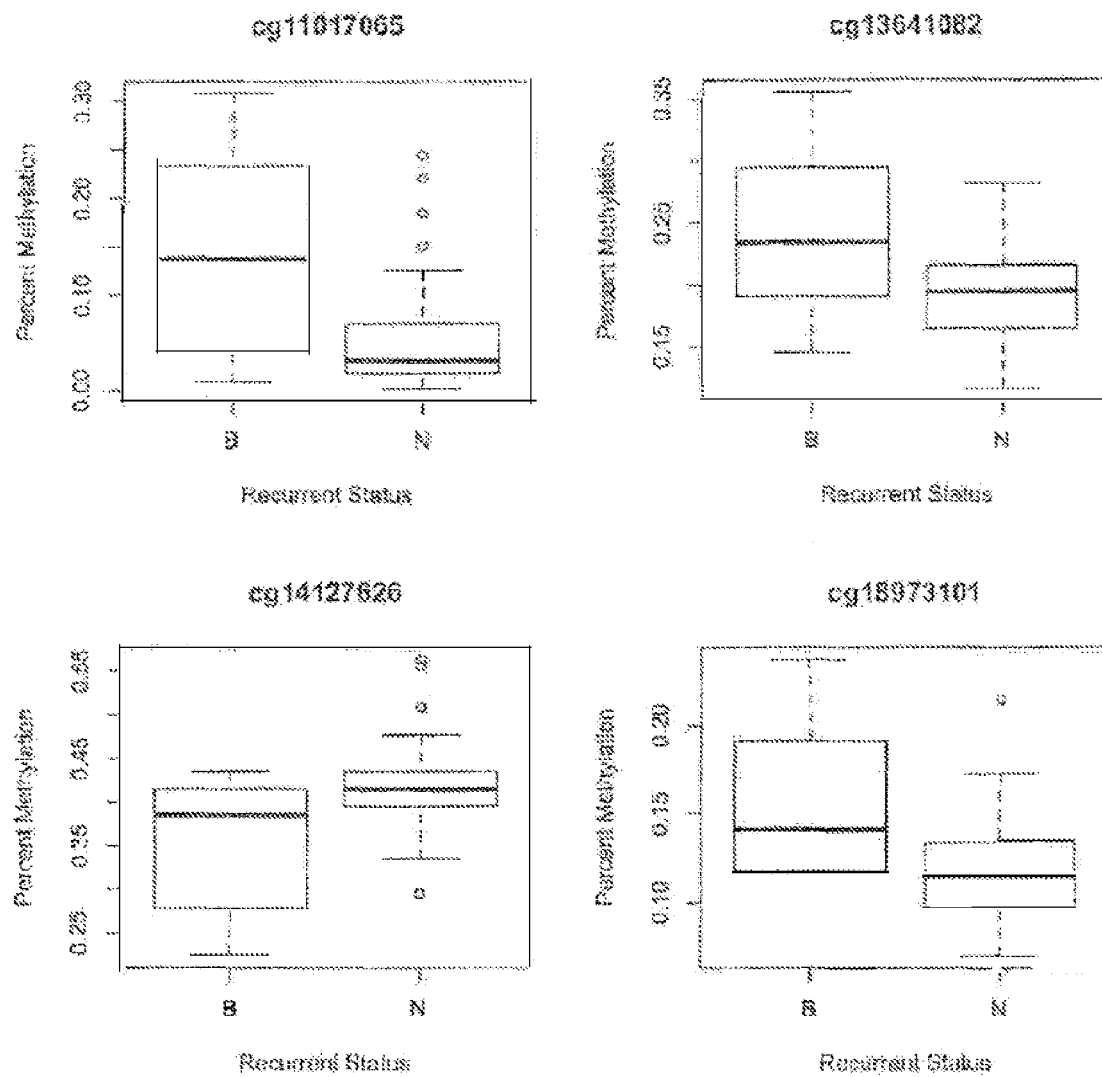
Figure 1A:
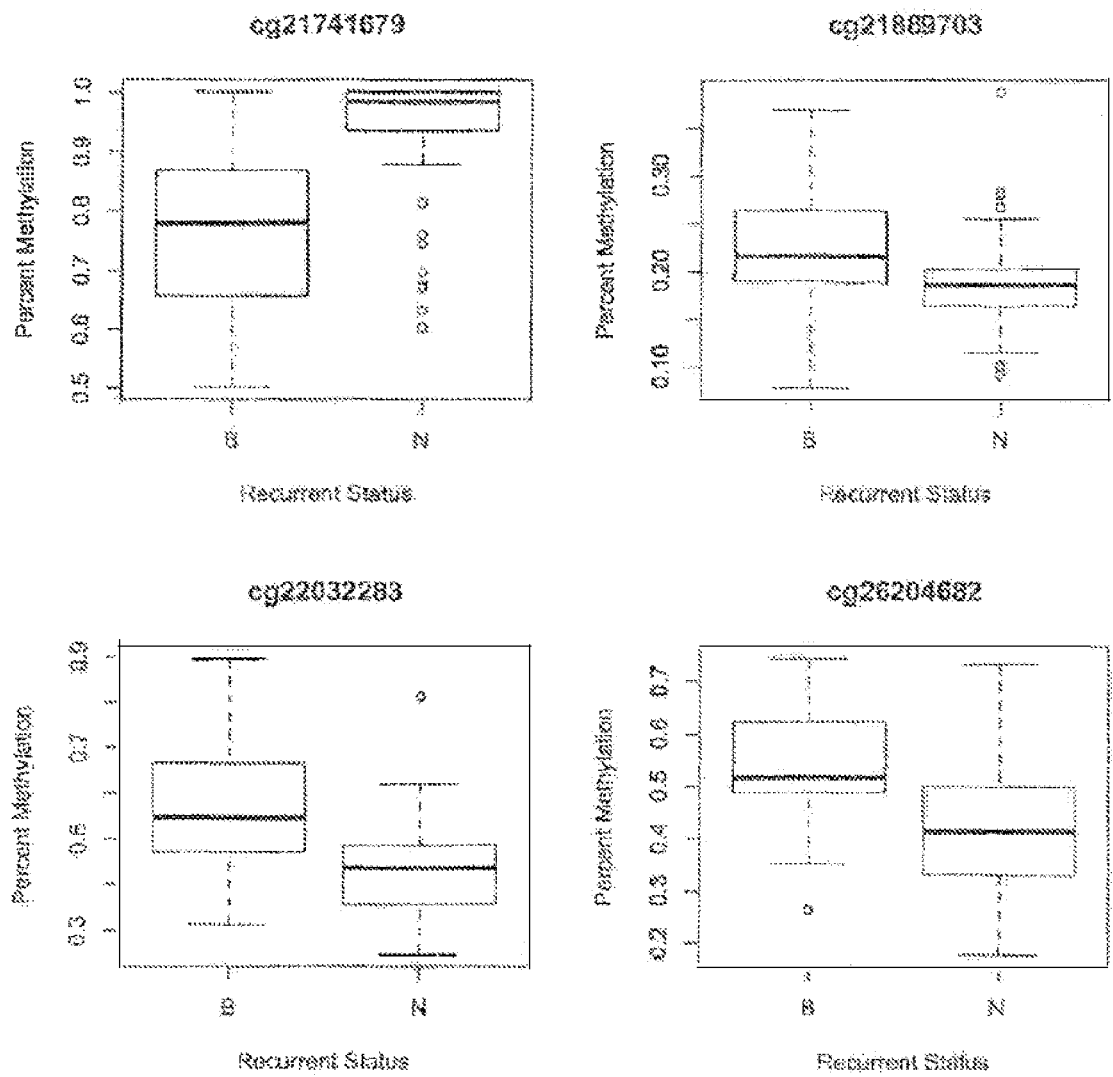
Figure 1A:
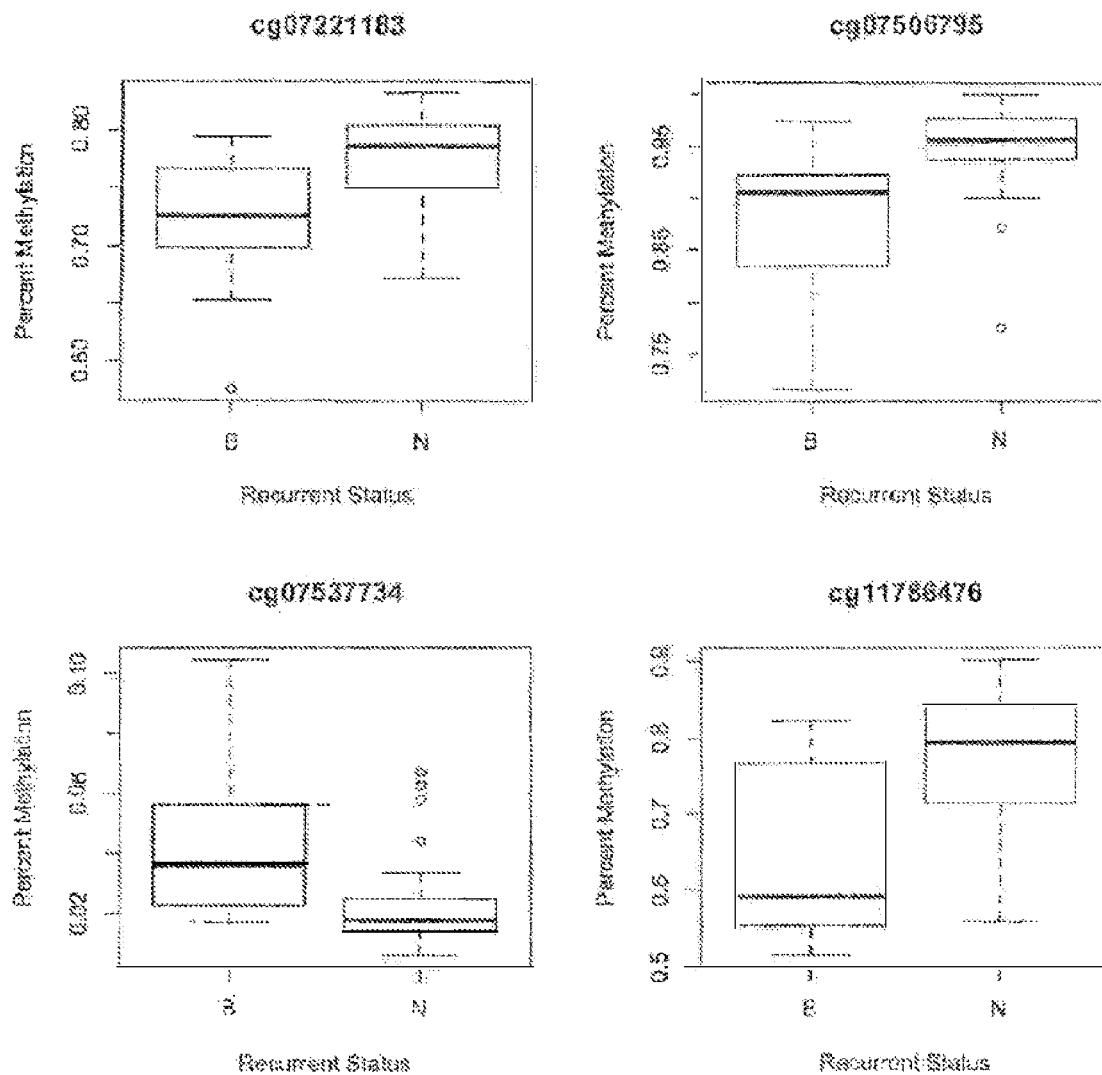
Figure 1A:
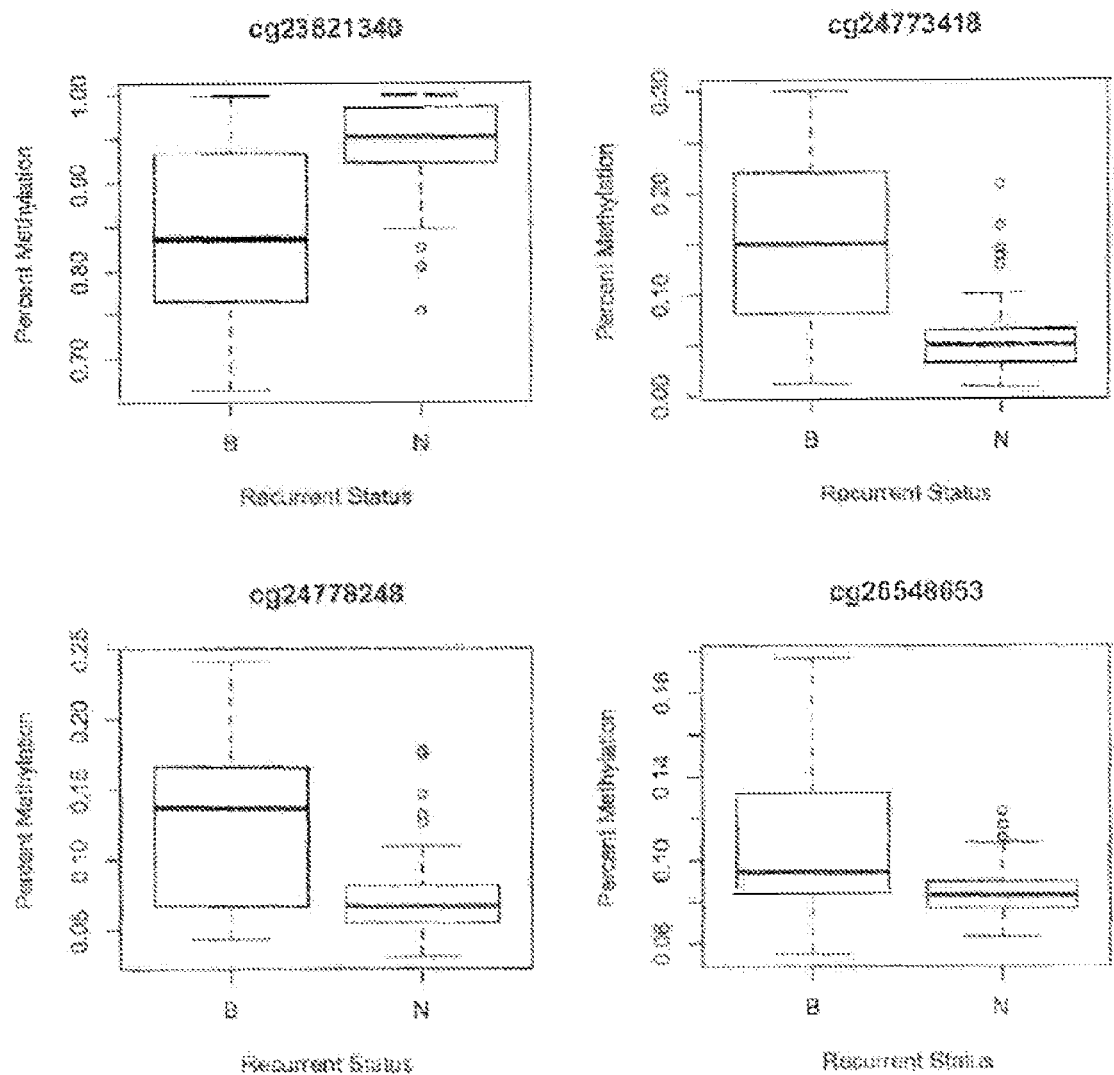
Figure 1B:
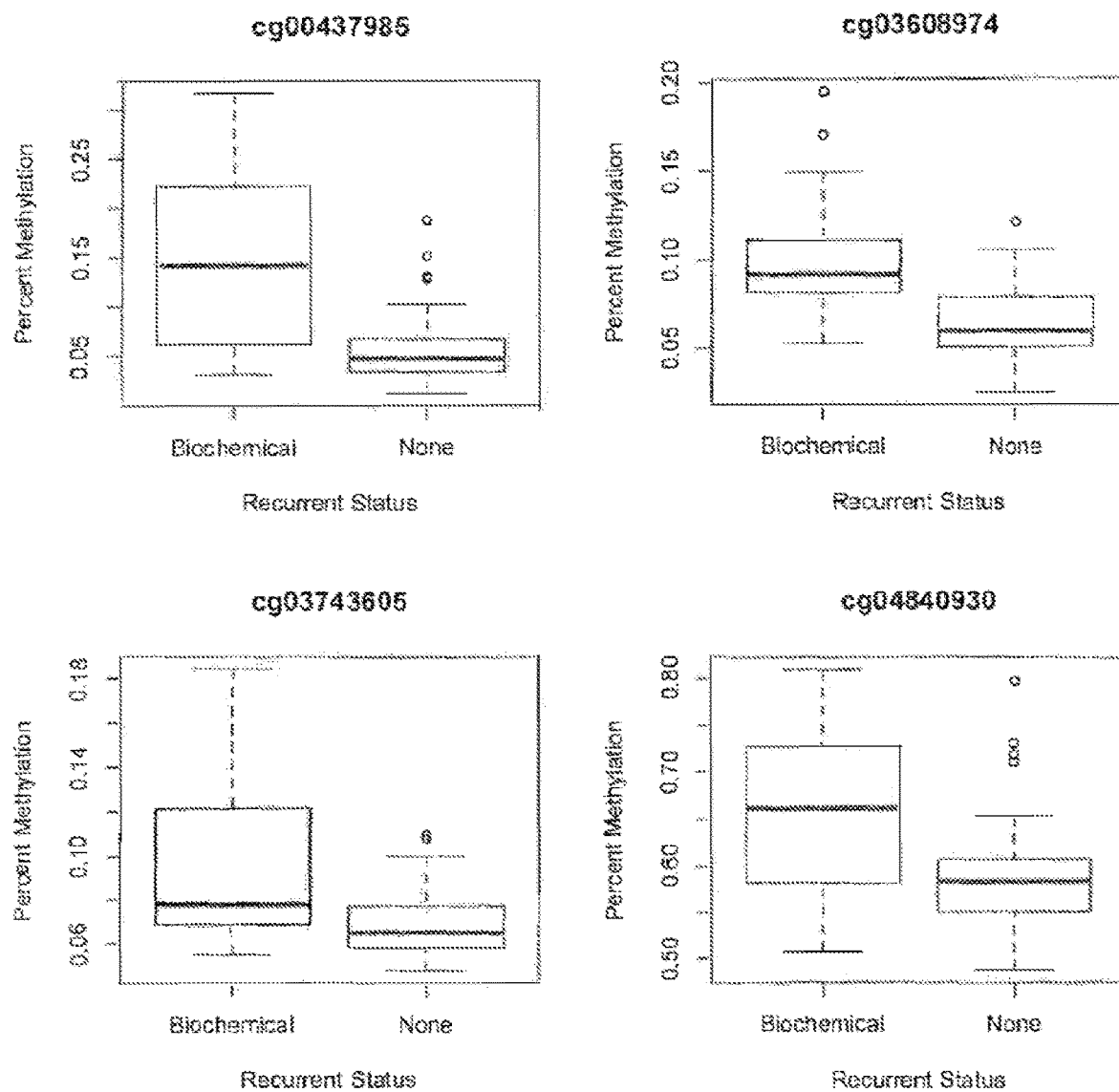
Figure 1B:
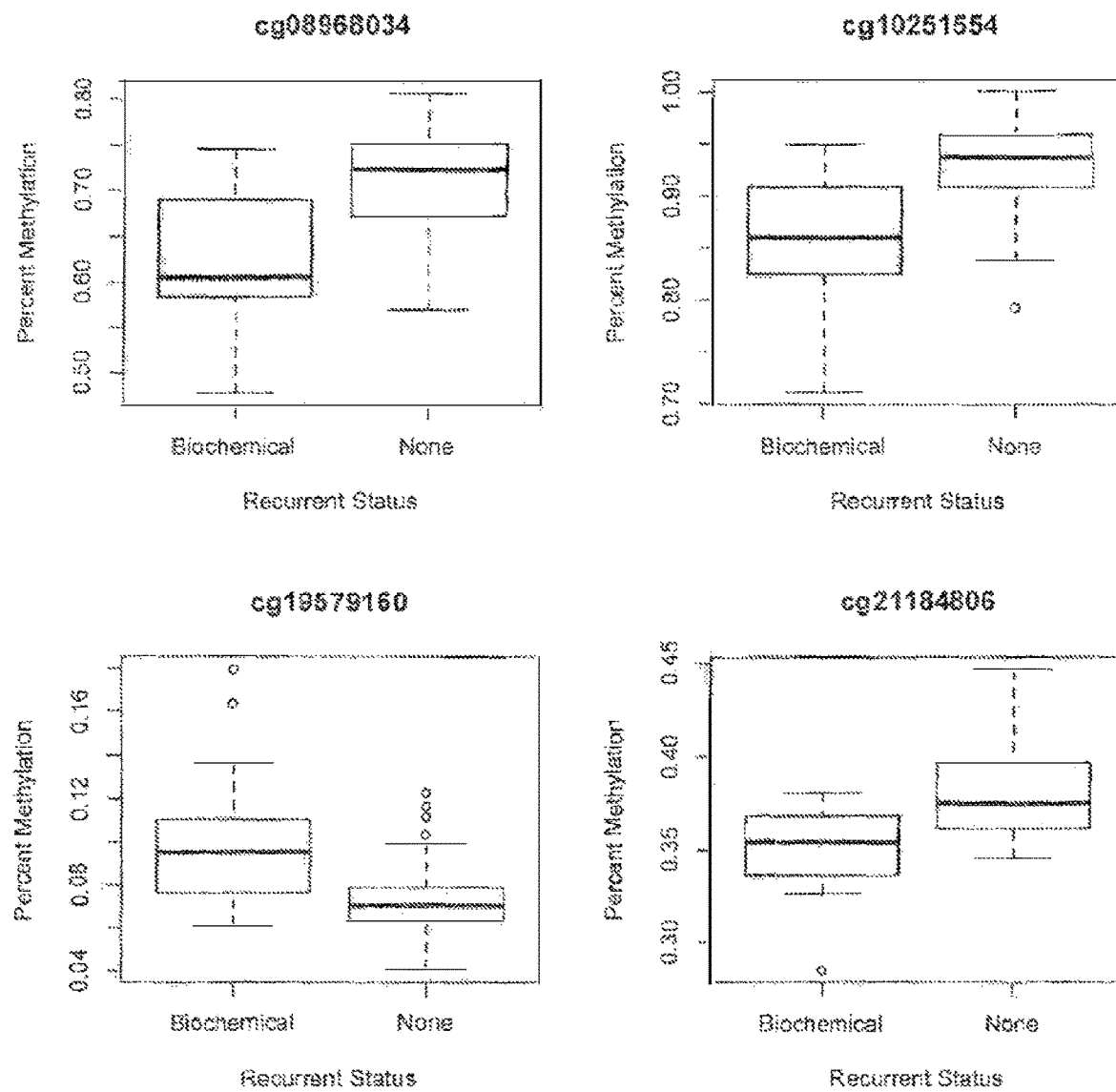
Figure 1B:
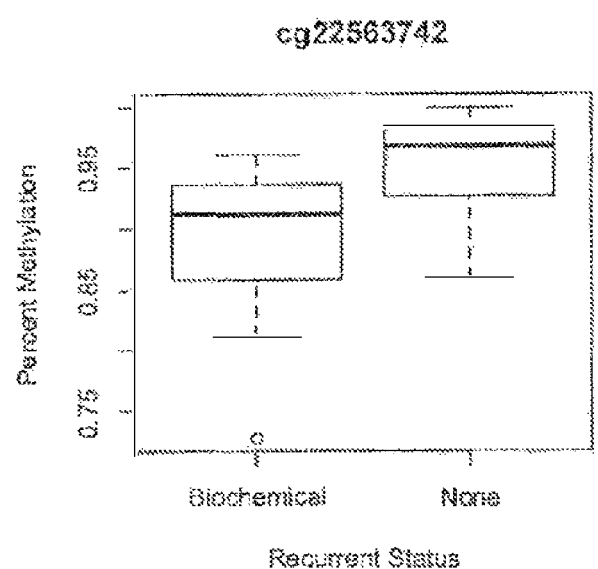
Figure 1C:
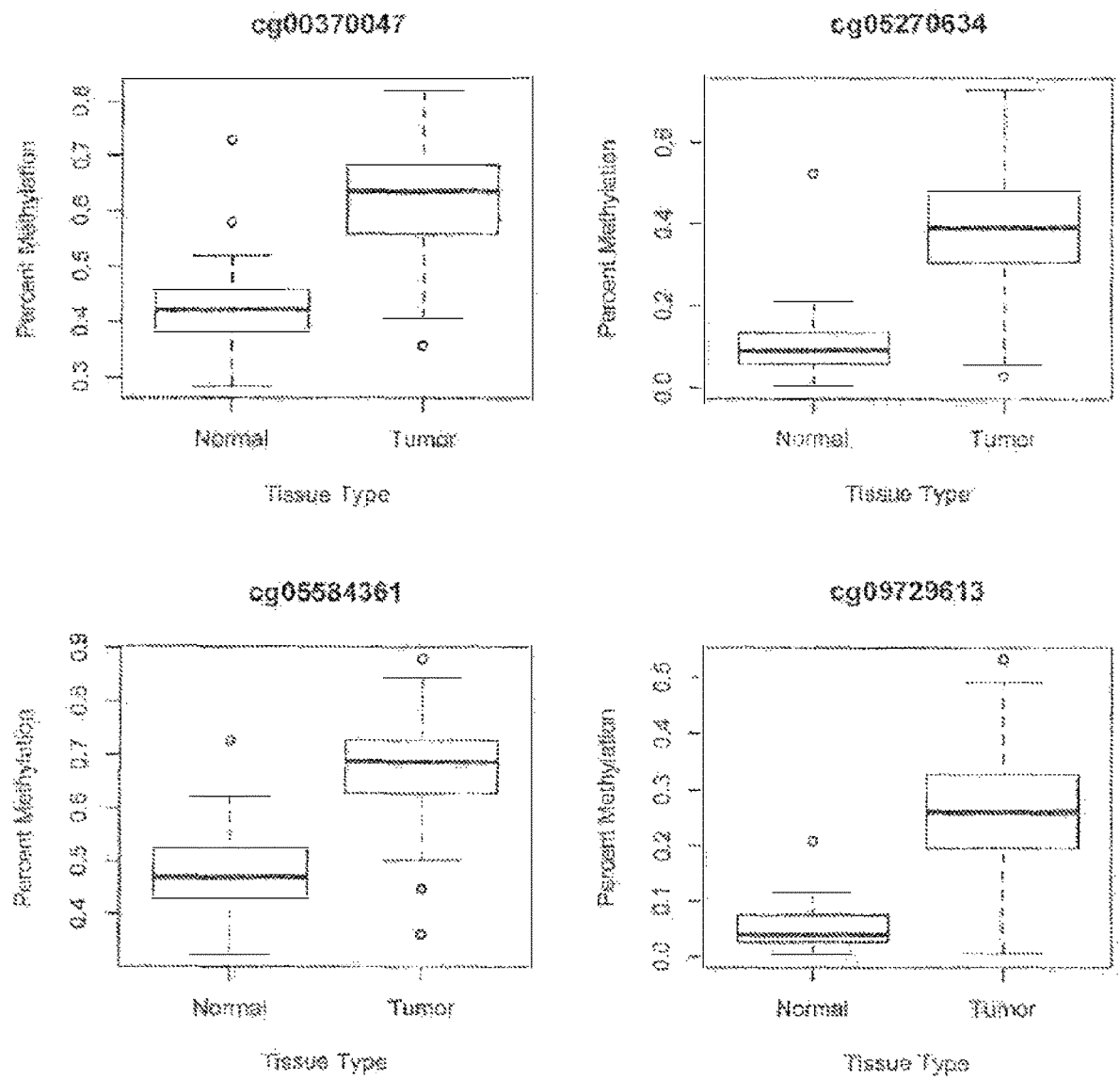
Figure 1C:
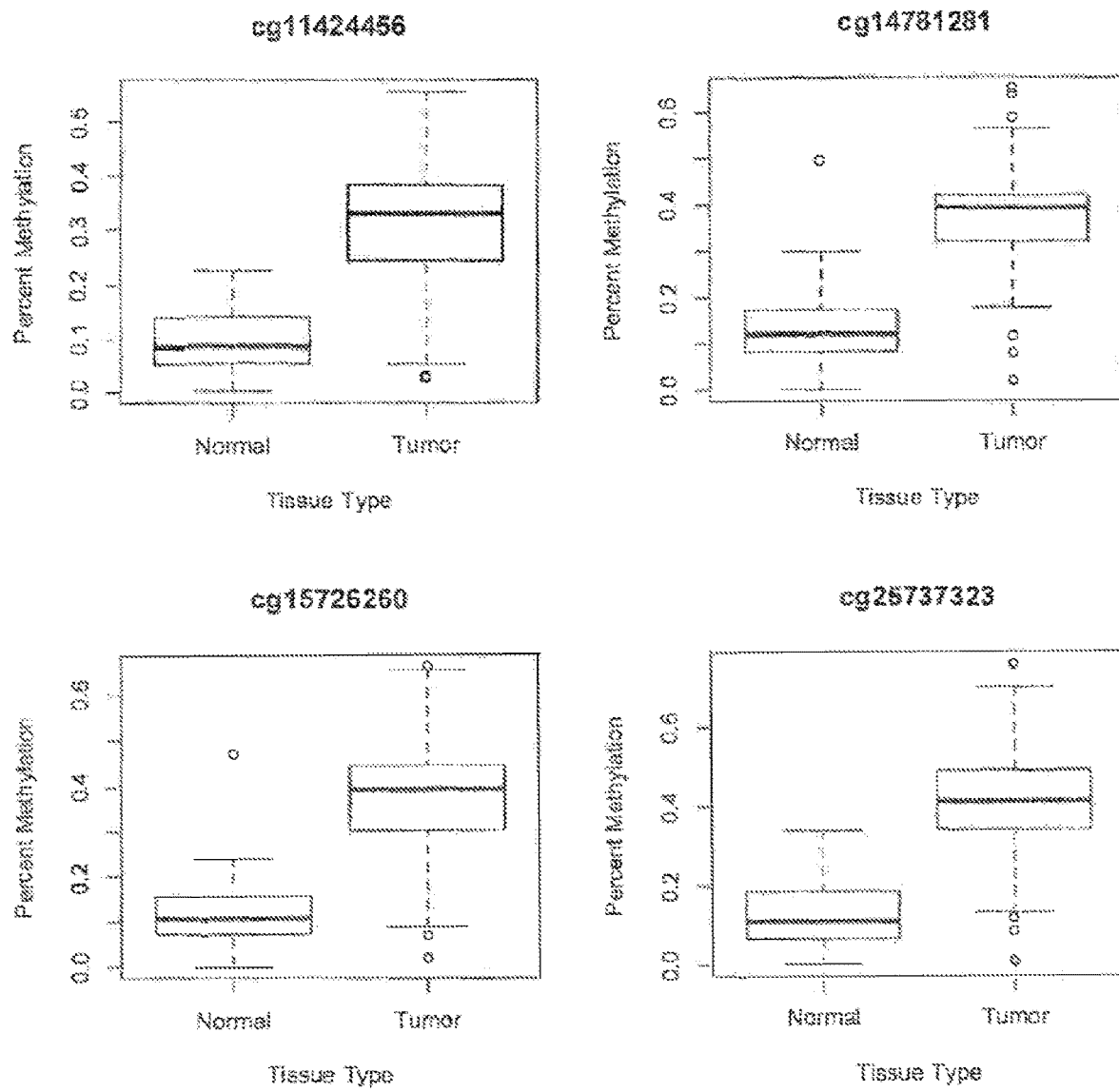
Figure 1C:
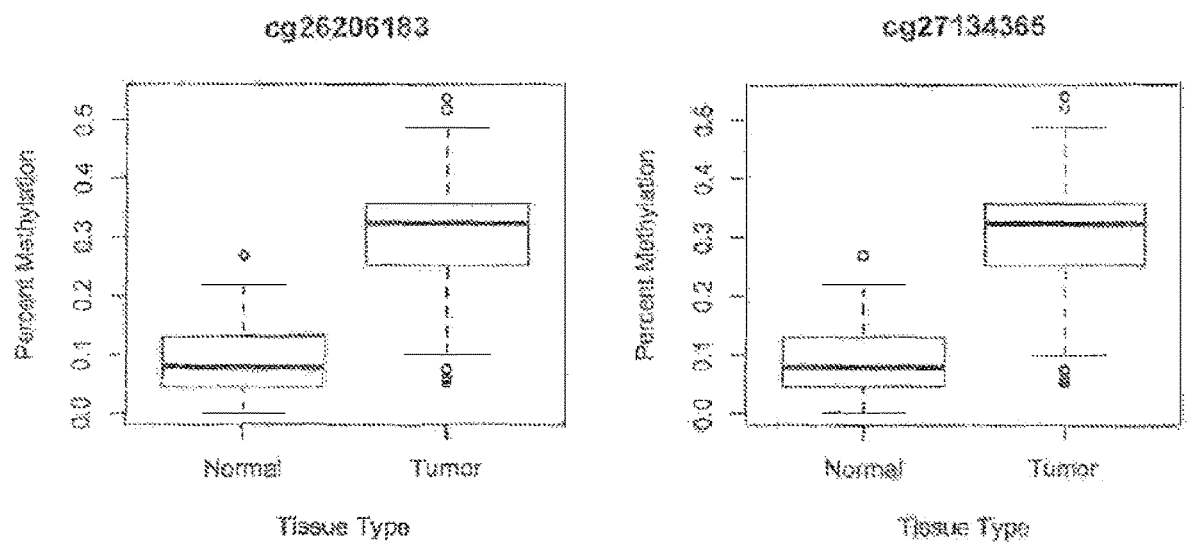

The present invention relates to the identification of novel biomarkers for diagnosis and prognosis of prostate cancer. The biomarkers of the invention are CpG loci that have altered methylation levels relative to normal prostate tissue, as set forth, for example, in Table 1. In one embodiment, the biomarkers are indicative of the biochemical reoccurrence of prostate cancer.

In some embodiments of the invention, the methylation level of one or a plurality of biomarkers set forth in Table 1 is determined in a patient sample suspected of comprising prostate cancer cells; wherein altered methylation at the indicated biomarker is indicative of prostate cancer or a biochemical recurrence of prostate cancer. In some embodiments, a plurality of biomarkers is evaluated for altered methylation.

In some embodiments the patient sample is a tumor biopsy. In other embodiments the patient sample is a convenient bodily fluid, for example a blood sample, urine sample, and the like. The biomarkers of the present invention may further be combined with other biomarkers for prostate cancer, including without limitation prostate specific antigen, chromosome copy number alterations, and the like.

DETAILED DESCRIPTION

Introduction

While the invention has been described with respect to a limited number of embodiments, those skilled in the art, having benefit of this disclosure, will appreciate that other embodiments can be devised which do not depart from the scope of the invention as disclosed here.

The present invention is based, in part, on the discovery that sequences in certain DNA regions are methylated in cancer cells, but not normal cells, or that methylation level at specific loci in prostate cancer patients that undergo biochemical recurrence have a different methylation level then the same loci in patients that do not undergo recurrence. Specifically, the inventors have found that methylation of biomarkers within the DNA regions described herein (such as those identified in Table 1) are associated with prostate cancer or the reoccurrence of prostate cancer.

In view of this discovery, the inventors have recognized that methods for detecting the biomarker sequences and DNA regions comprising the biomarker sequences as well as sequences adjacent to the biomarkers that contain CpG loci subsequences, methylation level of the DNA regions, and/or expression of the genes regulated by the DNA regions can be used to predict recurrence of cancer cells or to detect cancer cells. Detecting cancer cells allows for diagnostic tests that detect disease, assess the risk of contracting disease, determining a predisposition to disease, stage disease, diagnosis of disease, monitor disease, and/or prognostic biomarkers such as these methylation markers can be used to aid in the selection of treatment for a patient after prostatectomy.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al, Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques, if any, are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The "Gleason" grading system is used to help evaluate the prognosis of men with prostate cancer. Together with other parameters, it is incorporated into a strategy of prostate cancer staging, which predicts prognosis and helps guide therapy. A Gleason "score" or "grade" is given to prostate cancer based upon its microscopic appearance. Tumors with a low Gleason score typically grow slowly enough that they may not pose a significant threat to the patients in their lifetimes. These patients are monitored ("watchful waiting" or "active surveillance") over time. Cancers with a higher Gleason score are more aggressive and have a worse prognosis, and these patients are generally treated with surgery (e.g., radical prostectomy) and, in some cases, therapy (e.g., radiation, hormone, ultrasound, chemotherapy).

The term "individual" or "patient" as used herein refers to any animal, including mammals, such as, but not limited to, mice, rats, other rodents, rabbits, dogs, cats, swine, cattle, sheep, horses, primates, or humans.

The term "in need of prevention" as used herein refers to a judgment made by a caregiver that a patient requires or will benefit from prevention. This judgment is made based on a variety of factors that are in the realm of a caregiver's expertise, and may include the knowledge that the patient may become ill as the result of a disease state that is treatable by a compound or pharmaceutical composition of the disclosure.

The term "in need of treatment" as used herein refers to a judgment made by a caregiver that a patient requires or will benefit from treatment. This judgment is made based on a variety of factors that are in the realm of a caregiver's expertise, and may include the knowledge that the patient is ill as the result of a disease state that is treatable by a compound or pharmaceutical composition of the disclosure.

"Methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was methylated or methylated, respectively.

The term "methylation level" as applied to a gene refers to whether one or more cytosine residues present in a CpG context have or do not have a methylation group. Methylation level may also refer to the fraction of cells in a sample that do or do not have a methylation group on such cytosines. Methylation level may also alternatively describe whether a single CpG dinucleotide is methylated.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC (see, e.g., U.S. Pat. No. 5,405,760), McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., Nucleic Acids Res. 22(17):3640-59 (1994) and http://rebase.neb.com. Suitable methylation-sensitive restriction enzymes that do not cleave DNA at or near their recognition sequence when a cytosine within the recognition sequence is methylated include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae L, Eag L, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml1 I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N.sup.6 include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The term "prostate cancer" is used interchangeably and in the broadest sense refers to all stages and all forms of cancer arising from the tissue of the prostate gland.

The terms "peptide," "polypeptide," and "protein" each refer to a molecule comprising two or more amino acid residues joined to each other by peptide bonds. These terms encompass, e.g., native and artificial proteins, protein fragments and polypeptide analogs such as muteins, variants, and fusion proteins of a protein sequence as well as post-translationally, or otherwise covalently or non-covalently, modified proteins.

The terms "polynucleotide" and "nucleic acid" are used interchangeably throughout and include DNA molecules (e.g., cDNA or genomic DNA), RNA molecules (e.g., mRNA, siRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector.

The terms "prevent", "preventing", "prevention" "suppress", "suppressing" and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be useful.

The term "recurrence" is used herein to refer to local or distant recurrence (i.e., metastasis) of cancer. For example, prostate cancer can recur locally in the tissue next to the prostate or in the seminal vesicles. The cancer may also affect the surrounding lymph nodes in the pelvis or lymph nodes outside this area. Prostate cancer can also spread to tissues next to the prostate, such as pelvic muscles, bones, or other organs. Recurrence can be determined by clinical recurrence detected by, for example, imaging study or biopsy, or biochemical recurrence, which is defined by detectable PSA levels in the blood after prostatectomy.

The term "therapeutically effective amount", in reference to the treating, preventing or suppressing of a disease state, refers to an amount of a compound either alone or as contained in a pharmaceutical composition that is capable of having any detectable, positive effect on any symptom, aspect, or characteristics of the disease state/condition. Such effect need not be absolute to be beneficial.

The terms "treat", "treating" and "treatment" as used herein refers to administering a compound either alone or as contained in a pharmaceutical composition after the onset of clinical symptoms of a disease state so as to reduce or eliminate any symptom, aspect or characteristic of the disease state. Such treating need not be absolute to be useful.

DNA Methylation Level and Cancer

DNA methylation is a heritable, reversible and epigenetic change. Yet, DNA methylation has the potential to alter gene expression, which has profound developmental and genetic consequences. The methylation reaction involves flipping a target cytosine out of an intact double helix to allow the transfer of a methyl group from S adenosyl-methionine in a cleft of the enzyme DNA (cystosine-5)-methyltransferase to form 5-methylcytosine (5-mCyt). This enzymatic conversion is the most common epigenetic modification of DNA known to exist in vertebrates, and is essential for normal embryonic development.

The presence of 5-mCyt at CpG dinucleotides has resulted in a 5-fold depletion of this sequence in the genome during vertebrate evolution, presumably due to spontaneous deamination of 5-mCyt to T. Those areas of the genome that do not show such suppression are referred to as "CpG islands". These CpG island regions comprise about 1% of vertebrate genomes and also account for about 15% of the total number of CpG dinucleotides. CpG islands are typically between 0.2 to about 1 kb in length and are located upstream of many housekeeping and tissue-specific genes, but may also extend into gene coding regions. Therefore, the methylation levels of cytosine residues within CpG islands in somatic tissues can modulate gene expression throughout the genome. Methylation levels of cytosine residues contained within CpG islands of certain genes has been inversely correlated with gene activity. Thus, methylation of cytosine residues within CpG islands in somatic tissue is generally associated with decreased gene expression and can affect a variety of mechanisms including, for example, disruption of local chromatin structure, inhibition of transcription factor-DNA binding, or by recruitment of proteins which interact specifically with methylated sequences indirectly preventing transcription factor binding. Despite a generally inverse correlation between methylation of CpG islands and gene expression, most CpG islands on autosomal genes remain unmethylated in the germline and methylation of these islands is usually independent of gene expression. Tissue-specific genes are usually unmethylated at the receptive target organs but are methylated in the germline and in non-expressing adult tissues. CpG islands of constitutively-expressed housekeeping genes are normally unmethylated in the germline and in somatic tissues. A recent study showed evidence that methylation status of CpGs located within 2000 base pairs of a gene's transcription start site is negatively correlated with gene expression. For CpGs within a gene body, the methylation status of CpGs not in CpG islands is positively correlated with gene expression, whereas CpGs in the gene body in CpG islands can both negatively and positively impact gene expression (Varley et al 2013).

Abnormal methylation of CpG islands associated with tumor suppressor genes can cause altered gene expression. Increased methylation (hypermethylation) of such regions can lead to progressive reduction of normal gene expression resulting in the selection of a population of cells having a selective growth advantage. Conversely, decreased methylation (hypomethylation) of oncogenes can lead to modulation of normal gene expression resulting in the selection of a population of cells having a selective growth advantage. In some examples, hypermethylation and/or hypomethylation of one or more CpG dinucleotide is considered to be abnormal methylation.

Biomarkers

The present disclosure provides biomarkers useful for the detection of the prostate cancer or reoccurrence of prostate cancer, wherein the methylation level of the biomarker is indicative of the reoccurrence of prostate cancer. In one embodiment, the methylation level is determined by a cytosine. In one embodiment, the biomarkers are associated with certain genes in an individual. In one embodiment, the biomarkers are associated with certain CpG loci. In one embodiment, the CpG loci may be located in the promoter region of a gene, in an intron or exon of a gene or located near the gene in a patient's genomic DNA. In an alternate embodiment, the CpG may not be associated with any known gene or may be located in an intergenic region of a chromosome. In some embodiments, the CpG loci may be associated with one or more than one genes.

In one embodiment, the methylation level of one (1) of the following CpG loci may be determined (by any method set forth herein or known to those of skill in the art) to determine whether an individual is or may be at a risk for prostate cancer or a biochemical reoccurrence of prostate cancer: cg00474017, cg05387119, cg06161930, cg11017065, cg1364108, cg14127626, cg18973101, cg19480425, cg20077773, cg20522409, cg21889703, cg22032283, cg26204682, cg06345462, cg21139795, cg21741679, cg26450259, cg00054525, cg00175153, cg02945019, cg03724628, cg03862987, cg06353069, cg07198194, cg15126733, cg15338327, cg16515500, cg16794576, cg22059073, cg24033558, cg24581650, cg24922143, cg00437985, cg03608974, cg03743605, cg04840930, cg08968034, cg10251554, cg19579160, cg21184806, cg22563742, cg00370047, cg05270634, cg05584361, cg09729613, cg11424456, cg14781281, cg15726260, cg25737323, cg26206183, cg27134365, cg23821340, cg24778248, cg07537734, cg18472912, cg00004608, cg11786476, cg17881513, cg13916516, cg18516946, cg24773418, cg00493358, cg07221183, cg07506795, cg26548653 and cg27252467. In some aspects, the methylation level of two (2) or more or three (3) or more of the forgoing CpG loci may be determined (by any method set forth herein) to determine whether an individual is or may be at a risk for prostate cancer or a biochemical reoccurrence of prostate cancer.

In some aspects, the methylation level of two (2) or more or three (3) or more of the forgoing biomarkers be determined (by any method set forth herein) to determine whether a patient is or may be at a risk for prostate cancer or a biochemical reoccurrence of prostate cancer.

In one embodiment, an increase in the methylation level of one or more of the following CpG loci (and their corresponding SEQ ID NO.) is indicative of prostate cancer or the biochemical reoccurrence of prostate cancer: cg06161930; cg00370047; cg05270634; cg05584361; cg19579160; cg09729613; cg11424456; cg24922143; cg14781281; cg15726260; cg16794576; cg22059073; cg25737323; cg24033558; cg26206183; cg27134365; cg00054525; cg07198194; cg15338327; cg26548653; cg00437985; cg03608974; cg24778248; cg03743605; cg04840930; cg18973101; cg11017065; cg19480425; cg13641082; cg20522409; cg18472912; cg07537734; cg21139795; cg21889703; cg2477341.8; cg22032283; cg26204682; and cg00004608.

In one embodiment, a decrease in the methylation level of one or more of the following CpG loci (and their corresponding SEQ NOS.) is indicative of prostate cancer or the biochemical reoccurrence of prostate cancer: cg00474017, cg03724628, cg05387119, cg11017065, cg18973101, cg22563742, cg24581650, cg15126733, cg20522409, cg26204682, cg26450259, cg00493358, cg21741679, cg07221183, cg14127626, cg07506795, cg08968034, cg11786476, cg16515500, cg26450259, cg03862987, cg13916516, cg06345462, cg20077773, cg06353069, cg18516946, cg21184806, cg27252467, cg17881513, cg10251554, cg02945019, and cg23821340.

Table 1 shows the CpG loci, their chromosomal position (if known), and the genes associated with the CpG loci:

TABLE 1

| CpG loci | Chromosome | Associated Gene(s) | Position in Human Genome 19 (hg19) | SEQ ID NO. |
|---|---|---|---|---|
| cg00474017 | 13 | ADPRHL1 | 114074435 | SEQ ID NO. 1 |
| cg05387119 | 13 | ADPRHL1 | 114074465 | SEQ ID NO. 2 |
| cg06161930 | 19 | ZNF787 | 56633191 | SEQ ID NO. 3 |
| cg06345462 | 16 | SHISA9 | 13263104 | SEQ ID NO. 4 |
| cg11017065 | 11 | FLI1 | 128564874 | SEQ ID NO. 5 |
| cg13641082 | 7 | SNX8 | 2319604 | SEQ ID NO. 6 |
| cg14127626 | 9 | FANCC | 98075481 | SEQ ID NO. 7 |
| cg18973101 | 1 | SMG5; TMEM79 | 156251280 | SEQ ID NO. 8 |
| cg19480425 | 22 | NA | 22339538 | SEQ ID NO. 9 |
| cg20077773 | 12 | NA | 46851689 | SEQ ID NO. 10 |
| cg20522409 | X | AMMECR1; RGAG1 | 109661602 | SEQ ID NO. 11 |
| cg21139795 | 3 | CD80; TIMMDC1 | 119243933 | SEQ ID NO. 12 |
| cg21741679 | 2 | MYT1L | 2176774 | SEQ ID NO. 13 |
| cg21889703 | 6 | BCLAF1 | 136607649 | SEQ ID NO. 14 |
| cg22032283 | 13 | ARHGEF7 | 111936044 | SEQ ID NO. 15 |
| cg26204682 | 4 | NA | 105781484 | SEQ ID NO. 16 |
| cg26450259 | 10 | C10orf28 | 99912042 | SEQ ID NO. 17 |
| cg27252467 | 13 | LOC348021 | 19585665 | SEQ ID NO. 18 |
| cg00004608 | 6 | TBPL1 | 134272463 | SEQ ID NO. 19 |
| cg00493358 | 16 | CBFA2T3 | 88980724 | SEQ ID NO. 20 |
| cg07221183 | 16 | ZNF276 | 89800359 | SEQ ID NO. 21 |
| cg07506795 | 16 | ZNF19 | 71523560 | SEQ ID NO. 22 |
| cg07537734 | 4 | PDGFC | 157893541 | SEQ ID NO. 23 |
| cg11786476 | 6 | HLA-DPB2 | 33096738 | SEQ ID NO. 24 |
| cg13916516 | 9 | EXD3 | 140268774 | SEQ ID NO. 25 |
| cg17881513 | 8 | NA | 10717687 | SEQ ID NO. 26 |

TABLE 1-continued

| CpG loci | Chromosome | Associated Gene(s) | Position in Human Genome 19 (hg19) | SEQ ID NO. |
|---|---|---|---|---|
| cg18472912 | 5 | WWC1 | 167799541 | SEQ ID NO. 27 |
| cg18516946 | 11 | NA | 94774414 | SEQ ID NO. 28 |
| cg23821340 | 1 | PRDM16 | 3303053 | SEQ ID NO. 29 |
| cg24773418 | 14 | NA | 33402512 | SEQ ID NO. 30 |
| cg24778248 | 2 | CNGA3 | 98963062 | SEQ ID NO. 31 |
| cg26548653 | 19 | TMEM145; MEGF8 | 42829042 | SEQ ID NO. 32 |
| cg00054525 | 16 | CYBA | 88717587 | SEQ ID NO. 33 |
| cg00175153 | 16 | SNORA10; RPS2 | 2012763 | SEQ ID NO. 34 |
| cg02945019 | 1 | CD84 | 160550488 | SEQ ID NO. 35 |
| cg03724628 | 19 | RPS15 | 1440260 | SEQ ID NO. 36 |
| cg03862987 | 4 | G3BP2 | 76596784 | SEQ ID NO. 37 |
| cg06353069 | 2 | RAB17 | 238500081 | SEQ ID NO. 38 |
| cg07198194 | 10 | PFKP | 3109053 | SEQ ID NO. 39 |
| cg15126733 | 11 | RASSF7; C11orf35 | 562188 | SEQ ID NO. 40 |
| cg15338327 | 10 | NA | 101280209 | SEQ ID NO. 41 |
| cg16515500 | 18 | MC5R | 13826508 | SEQ ID NO. 42 |
| cg16794576 | 6 | NCRNA00171; HLA-J | 29974971 | SEQ ID NO. 43 |
| cg22059073 | 22 | CECR6 | 17602570 | SEQ ID NO. 44 |
| cg24033558 | 15 | SHF | 45479755 | SEQ ID NO. 45 |
| cg24581650 | 5 | ERGIC1 | 172263112 | SEQ ID NO. 46 |
| cg24922143 | 15 | NA | 35014270 | SEQ ID NO. 47 |
| cg00437985 | 16 | CRYM | 21295255 | SEQ ID NO. 48 |
| cg03608974 | 2 | ZAK | 173940268 | SEQ ID NO. 49 |
| cg03743605 | 1 | TOR3A | 179050691 | SEQ ID NO. 50 |
| cg04840930 | 6 | HYMAI; PLAGL1 | 144329997 | SEQ ID NO. 51 |
| cg08968034 | 4 | GRK4 | 3022836 | SEQ ID NO. 52 |
| cg10251554 | 7 | PAX4 | 127251442 | SEQ ID NO. 53 |
| cg19579160 | 2 | ZAK | 173940277 | SEQ ID NO. 54 |
| cg21184806 | 22 | NA | 34921399 | SEQ ID NO. 55 |
| cg22563742 | 12 | IQSEC3 | 185946 | SEQ ID NO. 56 |
| cg00370047 | 11 | BRSK2 | 1481436 | SEQ ID NO. 57 |
| cg05270634 | 17 | RND2 | 41177445 | SEQ ID NO. 58 |
| cg05584361 | 11 | BRSK2 | 1481525 | SEQ ID NO. 59 |
| cg09729613 | 2 | AOX1 | 201450601 | SEQ ID NO. 60 |
| cg11424456 | 17 | NA | 1131878 | SEQ ID NO. 61 |
| cg14781281 | 6 | NCRNA00171; HLA-J | 29974868 | SEQ ID NO. 62 |
| cg15726260 | 6 | NCRNA00171; HLA-J | 29974900 | SEQ ID NO. 63 |
| cg25737323 | 2 | CLIP4 | 29338100 | SEQ ID NO. 64 |
| cg26206183 | 14 | DHRS4L2 | 24457993 | SEQ ID NO. 65 |
| cg27134365 | 14 | DHRS4L2 | 24458004 | SEQ ID NO. 66 |

The biomarkers of the present disclosure.
The "CpG loci" column is the reference number provided by Illumina's ® Golden Gate and Infinium ® Assays.
The "position" column are the genomic positions that correspond to the most current knowledge of the human genome sequence which is the Human February 2009 assembly known as GRCh37/hg19.
The nucleotide sequences of the CpG loci in Table 1 are shown in Table 2 as well as the sequence listing tiled herewith.

Use of Biomarkers

In some embodiments, the methylation level of the chromosomal DNA within a DNA region or portion thereof (e.g., at least one cytosine residue) selected from the CpG loci identified in Table 1 is determined. In some embodiments, the methylation level of all cytosines within at least 20, 50, 100, 200, 500 or more contiguous base pairs of the CpG loci is also determined. For example, in one embodiment, the methylation level of the cytosine at cg18472912 is determined. In some embodiments, pluralities of CpG loci are assessed and their methylation level determined.

In some embodiments of the invention, the methylation level of a CpG loci is determined and then normalized (e.g., compared) to the methylation of a control locus. Typically the control locus will have a known, relatively constant, methylation level. For example, the control sequence can be previously determined to have no, some or a high amount of methylation (or methylation level), thereby providing a relative constant value to control for error in detection methods, etc., unrelated to the presence or absence of cancer. In some embodiments, the control locus is endogenous, i.e., is part of the genome of the individual sampled. For example, in mammalian cells, the testes-specific histone 2B gene (hTH2B in human) gene is known to be methylated in all somatic tissues except testes. Alternatively, the control locus can be an exogenous locus, i.e., a DNA sequence spiked into the sample in a known quantity and having a known methylation level.

The methylation sites in a DNA region can reside in non-coding transcriptional control sequences (e.g. promoters, enhancers, etc.) or in coding sequences, including introns and exons of the associated genes. In some embodiments, the methods comprise detecting the methylation level in the promoter regions (e.g., comprising the nucleic acid sequence that is about 1.0 kb, 1.5 kb, 2.0 kb, 2.5 kb, 3.0 kb, 3.5 kb or 4.0 kb 5' from the transcriptional start site through to the transcriptional start site) of one or more of the associated genes identified in Table 1.

Any method for detecting methylation levels can be used in the methods of the present invention.

In some embodiments, methods for detecting methylation levels include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. Alternatively, the method can encompass amplifying intact DNA after restriction enzyme digestion, thereby only amplifying DNA that was not cleaved by the restriction enzyme in the area amplified. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The methylation level of a CpG loci can be determined by providing a sample of genomic DNA comprising the CpG locus, cleaving the DNA with a restriction enzyme that is either methylation-sensitive or methylation-dependent, and then quantifying the amount of intact DNA or quantifying the amount of cut DNA at the locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample.

Kits for the above methods can include, e.g., one or more of methylation-dependent restriction enzymes, methylation-sensitive restriction enzymes, amplification (e.g., PCR) reagents, probes and/or primers.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602. Amplifications may be monitored in "real time."

Additional methods for detecting methylation levels can involve genomic sequencing before and after treatment of the DNA with bisulfite. When sodium bisulfite is contacted to DNA, unmethylated cytosine is converted to uracil, while methylated cytosine is not modified. Such additional embodiments include the use of array-based assays such as the Illumina® Human Methylation450 BeadChip and multiplex PCR assays. In one embodiment, the multiplex PCR assay is Patch PCR. PatchPCR can be used to determine the methylation level of a certain CpG loci. See Varley K E and Mitra R D (2010). Bisulfite Patch PCR enables multiplexed sequencing of promoter methylation across cancer samples. Genome Research. 20:1279-1287.

In some embodiments, restriction enzyme digestion of PCR products amplified from bisulfite-converted DNA is used to detect DNA methylation levels.

In some embodiments, a "MethyLight" assay is used alone or in combination with other methods to detect methylation level. Briefly, in the MethyLight process, genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, an Ms-SNuPE (Methylation-sensitive Single Nucleotide Primer Extension) reaction is used alone or in combination with other methods to detect methylation level. The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA.

Additional methylation level detection methods include, but are not limited to, methylated CpG island amplification and those described in, e.g., U.S. Patent Publication 2005/0069879; Rein, et al. Nucleic Acids Res. 26 (10): 225564 (1998); Olek, et al, Nat. Genet. 17(3): 275-6 (1997); and PCT Publication No. WO 00/70090.

Kits

This invention also provides kits for the detection and/or quantification of the diagnostic biomarkers of the invention, or expression or methylation level thereof using the methods described herein.

For Kits for detection of methylation level can comprise at least one polynucleotide that hybridizes to one of the CpG loci identified in Table 1 (or a nucleic acid sequence at least 90% identical to the CpG loci of Tale 1), or that hybridizes to a region of DNA flanking one of the CpG identified in Table 1, and at least one reagent for detection of gene methylation. Reagents for detection of methylation include, e.g., sodium bisulfite, polynucleotides designed to hybridize to sequence that is the product of a biomarker sequence of the invention if the biomarker sequence is not methylated, and/or a methylation-sensitive or methylation-dependent restriction enzyme. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region where the DNA region includes one of the CpG Loci identified in Table 1. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite, Methods of Diagnosis and Methods of Treatment The present disclosure provides methods for the treatment and/or prevention of a disease state that is characterized, at least in part, by the altered methylation level of the CpG loci identified in Table 1.

In one embodiment, the altered methylation at CpG loci are associated with the occurrence in a patient of a cancer. In one embodiment, the cancer is prostate cancer. In one embodiment, the altered methylation levels of the CpG loci are associated with the reoccurrence of prostate cancer. In one embodiment, the altered methylation levels of the CpG loci is differentially diagnostic in a patient suffering from prostate cancer as compared to a patient not suffering from prostate cancer.

As illustrated in FIGS. 1A-3, determining the methylation levels of at least one of the CpG loci identified in Table 1 is predictive of prostate cancer or the recurrence of prostate cancer. FIG. 1 shows that shows bar graphs of the percent methylation of each of the CpG loci in the biochemically recurrent patients and the non-recurrent patient where "B" is used for patients with a biochemical recurrence of prostate cancer and "N" is used for patients without a biochemical recurrence of prostate cancer.

Figure 2:
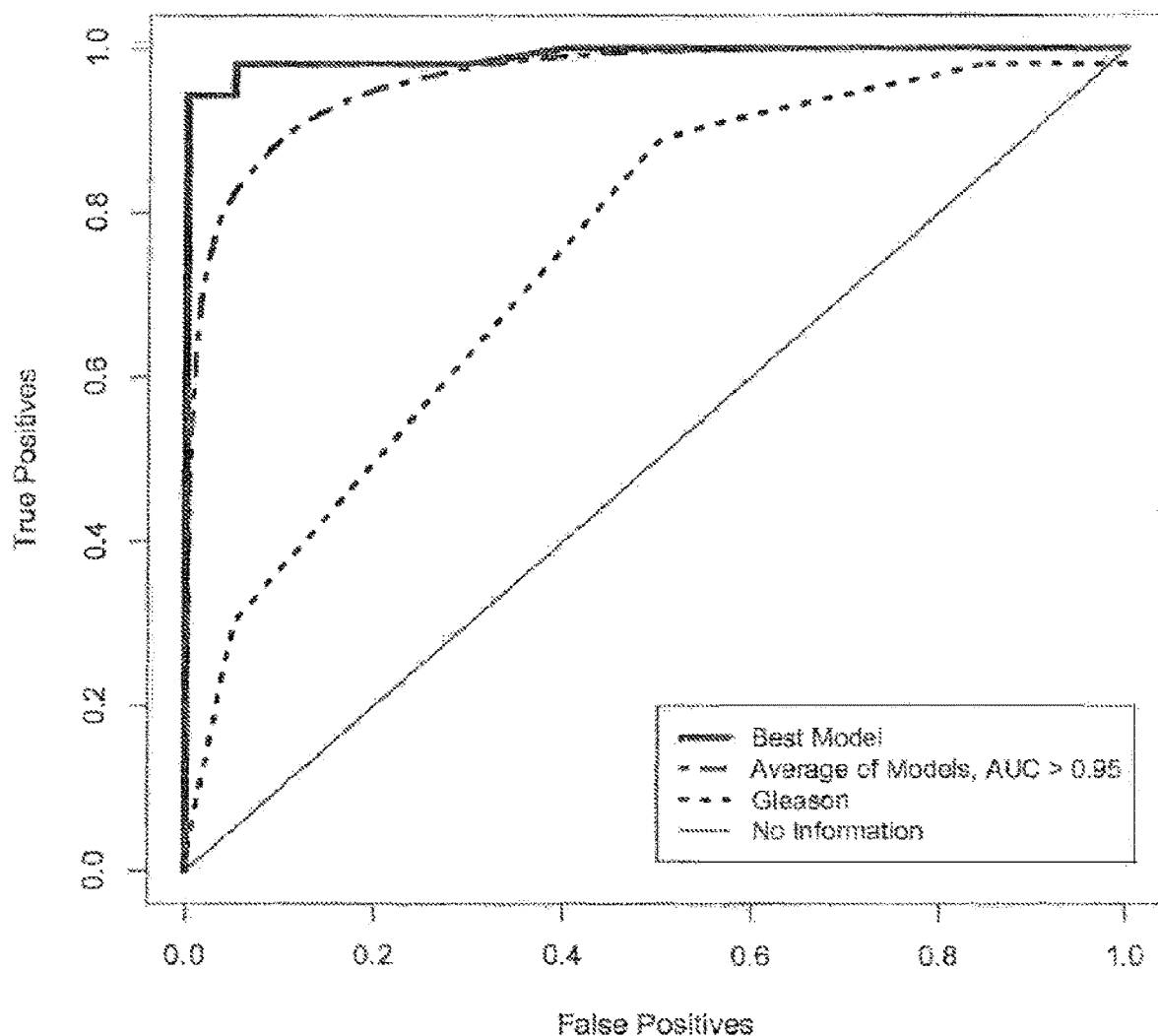
FIG. 2 shows the ROC curve for the best 3 CpG methylation model+Gleason grade from the 18 best predictive CpG loci found using linear regression (solid black line), the ROC curve for the average of all possible 3 CpG loci models from the 18 CpGs (dashes and circles), the ROC curve for Gleason grade alone (short dashes), and the ROC curve for something with no predictive power (thin black line). The ROC curve including both DNA methylation and Gleason grade (solid black line) is statistically significantly better (pval of 0.00031) at predicting patients who will biochemically recur over Gleason grade alone (black dashes).

FIG. 2 shows the ROC curve for the best 3 CpG methylation model+Gleason grade from the 18 CpGs found using linear regression (solid black line), the ROC curve for the average of all possible 3 CpG models from the 18 CpGs (dashes and circles), the ROC curve for Gleason grade alone (short dashes), and the ROC curve for something with no predictive power (thin black line). The ROC curve including both DNA methylation and Gleason grade (solid black line) is statistically significantly better (pval of 0.00031) at predicting patients who will biochemically recur over Gleason grade alone (black dashes).

Figure 3:
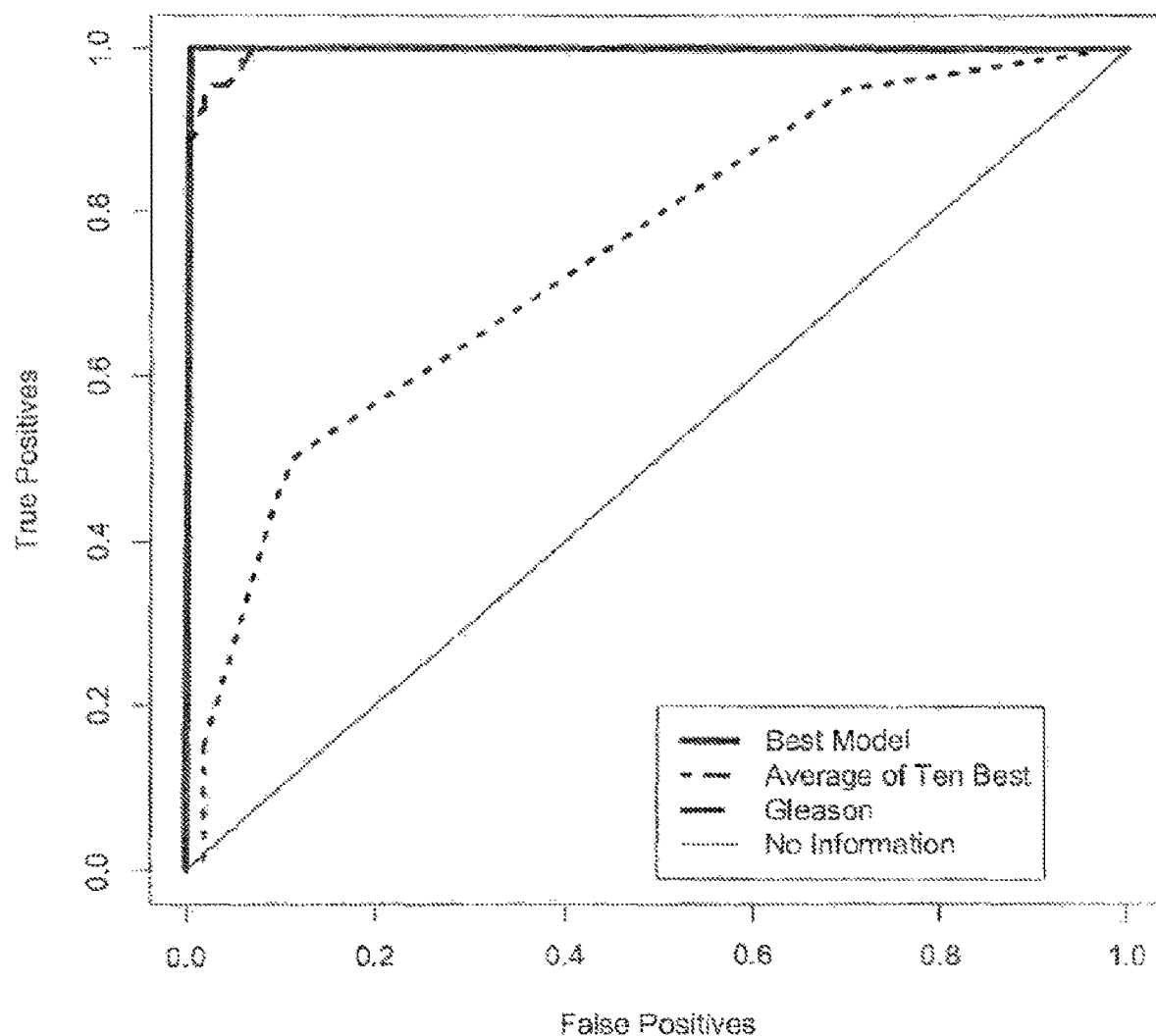
FIG. 3 shows the ROC curve models from the analysis of the predictive CpGs discovered using survival analysis. The solid black line shows the best predictive model of 3 CpG methylation values+Gleason grade out of the 100 CpGs tested, and this is a perfect predictor of recurrence in our dataset. The line with dashes and circles represents the average of the 10 best models from the 100 CpGs tested, the line with short dashes represents the predictive power of Gleason grade alone, and the black line represents a model with no predictive power.
Figure 4:
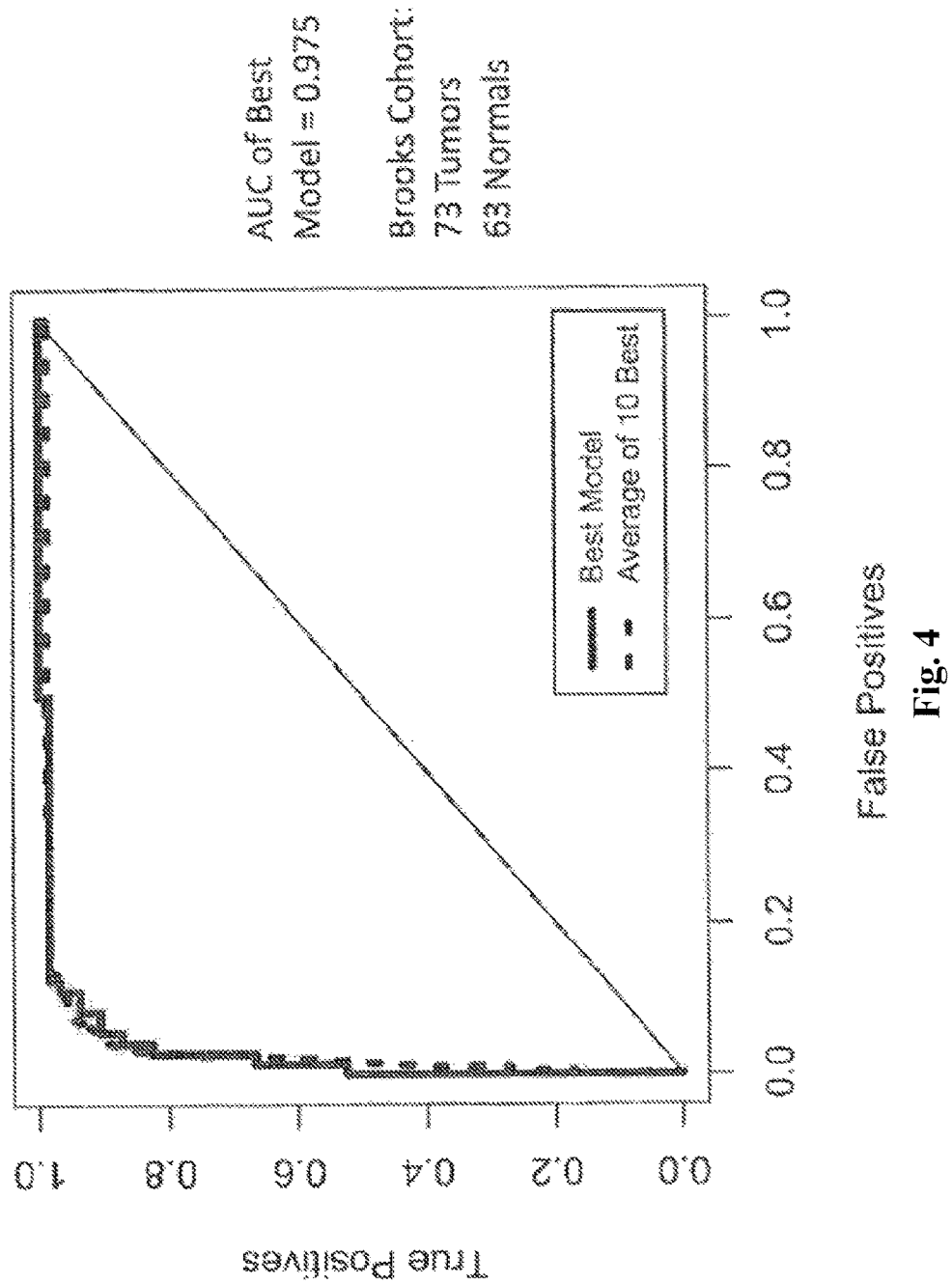
FIG. 4 shows the ROC curve model of the ten (10) best diagnostic models presented herein. The ROC curves from the best model (blue line), the average of the 10 best models (yellow dashed line), and all of the ROC curves from each 3 CpG model from the top 100 CpGs (blue haze) identified in linear mixed model.
Figure 5:
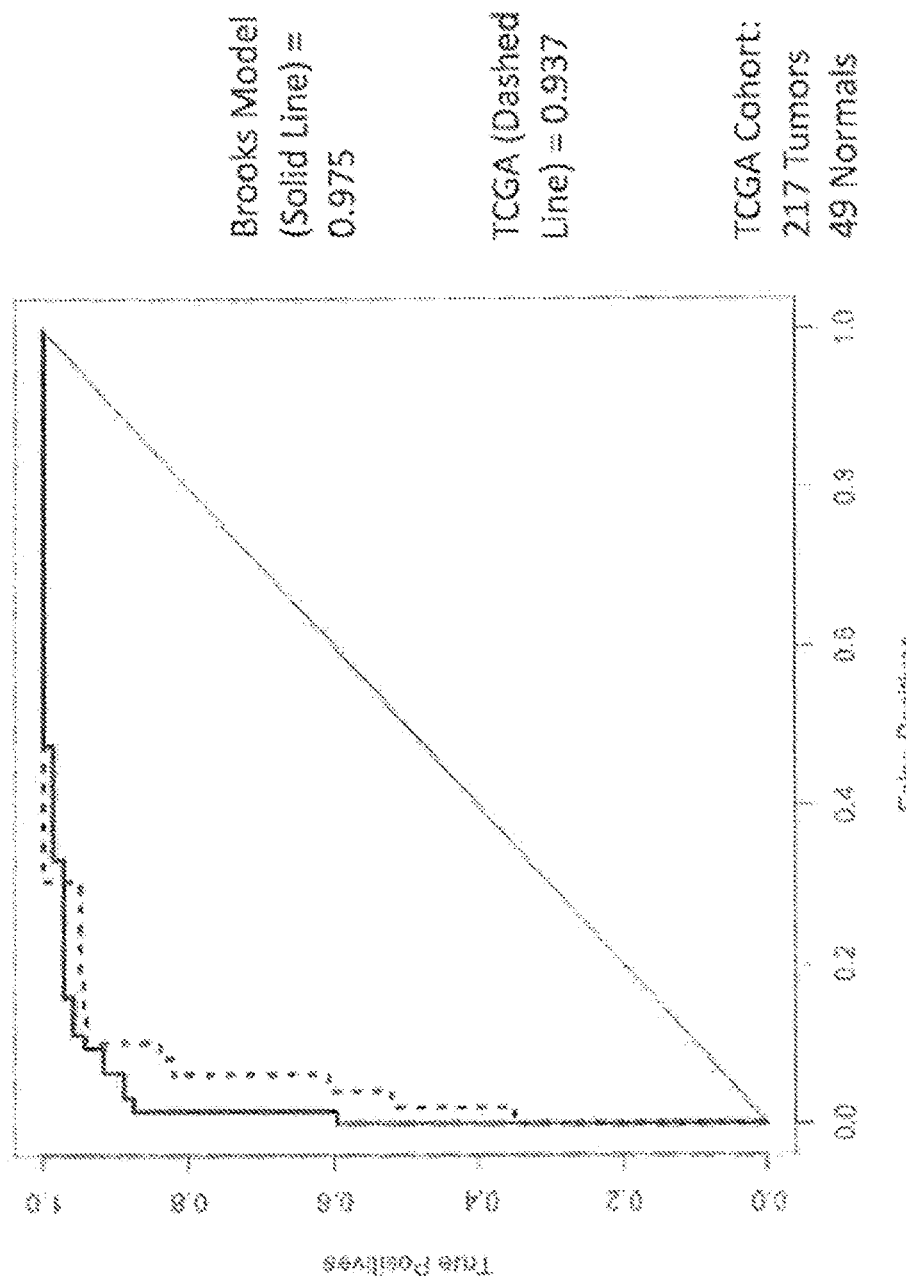
FIG. 5 shows a diagnostic ROC curve with TCGA validation curve: The ROC curve from the most predictive Diagnostic 3 CpG methylation model in our cohort of tissues (Brooks Model=Blue line; AUC=0.98), and that model applied to TCGA prostate methylation data (TCGA=Black line; AUC=0.93). The high AUC in both cohorts demonstrates the high ability of this DNA methylation model to distinguish prostate tumor tissue from benign-adjacent tissue.
Figure 6:
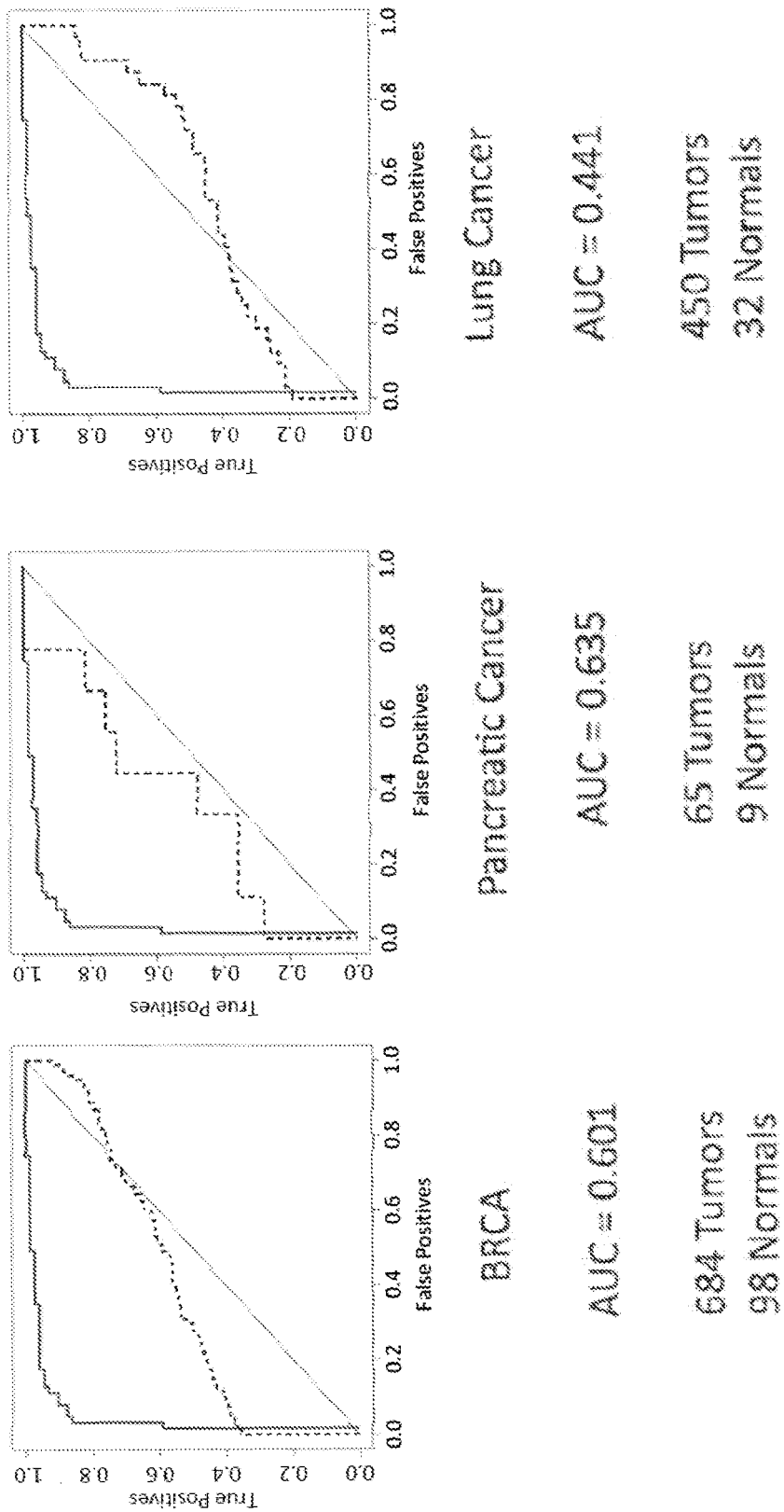
FIG. 6 shows the diagnostic model disclosed herein Applied To Other Cancer Types: The ROC curve from the most predictive Diagnostic 3 CpG methylation model in our cohort of tissues (Brooks Model=Blue line; AUC=0.93), and that model applied to TCGA methylation data from other cancer types (Breast, Pancreatic and Lung Cancer; AUC=0.6, 0.64, and 0.44 respectively). The low AUC of this methylation model in other cancer types suggests that this Diagnostic model is specific to prostate cancer.

FIG. 3 shows the ROC curve models from the analysis of the predictive CpGs discovered using survival analysis. The solid black line shows the best predictive model of 3 CpG methylation values+Gleason grade out of the 100 CpGs tested, and this is a perfect predictor of recurrence in our dataset. The line with dashes and circles represents the average of the 10 best models from the 100 CpGs tested, the line with short dashes represents the predictive power of Gleason grade alone, and the black line represents a model with no predictive power.

Other non-limiting methods of diagnosis and treatment are described below. In this embodiment, the methylation levels of the CpG loci identified in Table 1 is detected to aid in the treatment, prevention or diagnosis of a cancer, such as prostate cancer.

The steps in the method of treatment or prevention, in one embodiment are:

A. Identifying a patient in need of the prevention or treatment of prostate cancer. This identifying step may be accomplished by many different methods. The patient could be identified by a physician who believes the patient would benefit from such treatment prevention or by standard genetic screening or analysis indicating the patient would benefit from such treatment or prevention.

B. Obtaining a sample from the patient. In some embodiments the patient sample is a tumor biopsy. In other embodiments the patient sample is a convenient bodily fluid, for example a blood sample, urine sample, and the like. The sample may be obtained by other means as well.

C. Determining the methylation levels of one or more of the CpG loci or dinucleotides at the Hg19 positions identified on Table 1. This determination step may be accomplished by any of the means set forth in this disclosure. In one embodiment, the methylation level of one of the CpG loci is determined while in other embodiments, the methylation levels of a plurality of the CpG loci are determined. Additionally, other tests may be used in conjunction with this determining step, including without limitation PSA assays and the Gleason score.

D. Comparing the methylation levels of CpG loci determined in step "C" to a reference or control. In one embodiment, a methylation level of the CpG loci determined in step "C" different from the control is indictitive of the reoccurrence of prostate cancer. This comparison step may be accomplished by any of the methods set forth herein.

E. Treating the patient with a therapeutically effective amount of a composition or radiation therapy if the comparing step in "D" above indicates the reoccurrence of prostate cancer. In one embodiment, the composition may include compounds for hormone therapy such as androgen deprivation therapy.

In one embodiment, the method of treatment or prevention above is used if the patient has previously undergone treatment, such as radiation, a prostatectomy or hormone treatment for prostate cancer and a reoccurrence of prostate cancer is feared.

In an alternate embodiment, the present invention provides methods for determining the methylation status of an individual. In one aspect, the methods comprise obtaining a biological sample from an individual; and determining the methylation level of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOS.: 1-66.

In some embodiments, the methods comprise:

A. Determining the methylation status of at least one cytosine within a DNA region in a sample from the individual where the DNA region is at least 90%, 91%, 92%, 93%, 94%, 95%, 96%, 97%, 98%, or 99% identical to, or comprises, a sequence selected from the group consisting of SEQ ID NOS.: 1-66 and B. Comparing the methylation status of the at least one cytosine to a threshold value for the biomarker, wherein the threshold value distinguishes between individuals with and without cancer, wherein the comparison of the methylation status to the threshold value is predictive of the presence or absence of prostate cancer in the individual.

In some embodiments, the methods comprise:
A. Determining the methylation status of at least one cytosine within a DNA region in a sample from the individual where the DNA region is at least 90%, 91%, 92%, 93%, 94%, 95%, 96%, 97%, 98%, or 99% identical to, or comprises, a sequence selected from the group consisting of SEQ ID NOS.: 1-66 and
B. Comparing the methylation status of the at least one cytosine to a threshold value for the biomarker, wherein the threshold value distinguishes between individuals with and without cancer, wherein the comparison of the methylation status to the threshold value is predictive of the biochemical reoccurrence of prostate cancer in the individual.

Computer-Based Methods

The calculations for the methods described herein can involve computer-based calculations and tools. For example, a methylation level for a DNA region or a CpG loci can be compared by a computer to a threshold value, as described herein. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

In a further aspect, the invention provides computer implemented methods for determining the presence or absence of cancer (including but not limited to prostate cancer or the biochemical reoccurrence of prostate cancer) in an individual. In some embodiments, the methods comprise: receiving, at a host computer, a methylation value representing the methylation level of at least one cytosine within a DNA region in a sample from the individual where the DNA region is at least 90%, 91%, 92%, 93%, 94%, 95%, 96%, 97%, 98%, or 99% identical to, or comprises, a sequence is selected from the group consisting of SEQ ID NOS: 1-66; and comparing, in the host computer, the methylation level to a threshold value, wherein the threshold value distinguishes between individuals with and without cancer (including but not limited to prostate cancer or the biochemical reoccurrence of prostate cancer), wherein the comparison of the methylation level to the threshold value is predictive of the presence or absence of cancer (including but not limited to prostate cancer or the biochemical reoccurrence of prostate cancer) in the individual.

In some embodiments, the receiving step comprises receiving at least two methylation values, the two methylation values representing the methylation level of at least one cytosine biomarkers from two different DNA regions; and the comparing step comprises comparing the methylation values to one or more threshold value(s) wherein the threshold value distinguishes between individuals with and without cancer (including but not limited to prostate cancer or the biochemical reoccurrence of prostate cancer), wherein the comparison of the methylation value to the threshold value is predictive of the presence or absence of cancer (including but not limited to cancers of the bladder, breast, cervix, colon, endometrium, esophagus, head and neck, liver, lung(s), ovaries, prostate, rectum, and thyroid, and melanoma) in the individual.

In another aspect, the invention provides computer program products for determining the presence or absence of cancer (including but not limited to prostate cancer or the biochemical reoccurrence of prostate cancer), in an individual. In some embodiments, the computer readable products comprise: a computer readable medium encoded with program code, the program code including: program code for receiving a methylation value representing the methylation status of at least one cytosine within a DNA region in a sample from the individual where the DNA region is at least 90%, 91%, 92%, 93%, 94%, 95%, 96%, 97%, 98%, or 99% identical to, or comprises, a sequence selected from the group consisting of SEQ ID NOS: 1-66 and program code for comparing the methylation value to a threshold value, wherein the threshold value distinguishes between individuals with and without cancer (including but not limited to prostate cancer or the biochemical reoccurrence of prostate cancer), wherein the comparison of the methylation value to the threshold value is predictive of the presence or absence of cancer (including but not limited to prostate cancer or the biochemical reoccurrence of prostate cancer), in the individual.

Materials and Methods

Tissues/Nucleic Acid:

Prostate tissues used for this study were collected at Stanford University Medical Center between 1999 and 2007 with patient informed consent under an IRB-approved protocol. Tissue samples were removed from each prostate, flash-frozen, and stored at −80° C. Tumor tissue samples underwent macro-dissection to enrich for tumor cell population, and tumor tissues in which at least 90% of the epithelial cells were cancerous were selected for nucleic acid extractions. Nucleic acid was extracted from the tissues using QIAGEN AllPrep DNA/RNA mini kit (QIAGEN).

DNA Methylation Analysis via Illumina Infinium Human-Methylation 450K:

Five hundred nanograms of DNA from each tissue was sodium bisulfite treated, and DNA methylation levels were assayed using the Illumina Infinium HumanMethylation 450K beadchip array (Illumina). We calculated the methylation beta score as: $\beta = \text{Intensity}_{Methylated}/\text{Intensity}_{Methylated} + \text{Intensity}_{Unmethylated})$. We converted any data points that were not significantly above the background intensity to NAs. We removed any CpG with greater than 10% missing values. In order to correct for batch effect, we performed a Combat normalization on array chip number using the ComBat R package. Post-ComBat normalization, we observed that the Infinium I and II assays showed two distinct bimodal β-value distributions, so we developed a regression method to convert the type I and type II assays to a single bimodal β-distribution corresponding to Reduced Representation Bisulfite Sequencing (RRBS) β-values. This corrected for the distinct bimodal distributions and aligned our data with RRBS values to allow for future integration with RRBS data. We selected four samples to develop a regression equation to convert Methyl 450K data to RRBS data. We split the Combat normalized Methylation 450K data based on the type I or type II assay giving us 12,687 CpGs for the type I assay and 8,439 CpGs for the type II assay. We then developed a linear and quadric equation relating the Methylation 450 type I and type II assays β-values to the RRBS β-values using least-squares regression. After testing the equations and visual inspection of the RRBS vs. Methylation 450K-values scatter plots, we determined the quadric equation gave the best fit to the data. The β-value distribution is fixed at zero and one, thus after the Methylation 450K data was converted to RRBS β-values using the quadric equations, any values less than zero were assigned zeros and values greater than one were assigned ones. The equations for correction are shown below:

Infinium I to RRBS $$RRBS_\beta = 0.00209 + 0.4377 \times Methyl450_\beta + 0.6303 \times Methyl450_\beta^2$$

Infinium II to RRBS $$RRBS_\beta = 0.01146 + 0.2541 \times Methyl450_\beta + 0.9832 \times Methyl450_\beta^2$$

Discovery of CpG Loci with DNA Methylation Levels Statistically Associated with Biochemical Recurrence using Linear Regression Models:

Prior to any statistical analysis, in order to improve statistical power, we removed any CpG that had a standard deviation across all samples less than 0.01, as these CpGs were considered unchanged across samples. This left us with 347,899 CpGs for the statistical analysis. We fit the tumor prostate DNA methylation data to a linear model using the 1 m function in R. We included several clinical covariates in the linear model, including patient PSA level before prostatectomy surgery, patient pathological Gleason grade, T score (from TNM prostate staging score), N score from TNM prostate staging score), whether the patient had positive surgical margins or not, whether the tumor invaded the seminal vesicals, whether the tumor invaded the capsule of the prostate, and whether the patient is biochemically recurrent. At an FDR of 10%, we discovered 13 CpG loci that had DNA methylation patterns that were statistically associated with biochemical recurrence. We also fit the tumor prostate DNA methylation data to a Robust linear model using the rlm function in R. At an FDR of 5%, filtering out CpGs that did not converge, we found 1,222 CpG loci that had DNA methylation patterns that were statistically associated with biochemical recurrence. Because significant rlm results are prone to outliers, we further filtered the significant CpGs to highlight CpGs with the largest methylation differences between the biochemically recurrent patients and the non-recurrent patients. We selected, from the 1,222 CpG loci, CpGs with a median methylation difference between biochemical recurrent patients and non-recurrent patients of at least 10%, and a Median Absolute Deviation (meaning the dispersion of the data around the median) no greater than 20%. This filtering process left us with 5 additional CpGs over the 13 that we discovered through linear regression.

Discovery of CpG Loci with DNA Methylation Levels Statistically Associated with Biochemical Recurrence using Survival Analysis:

After the static regression analysis was completed we used survival analysis to include time to recurrence in our study. The time to recurrence data was censored; hence we used the Cox proportional hazards model to study the affect of CpG methylation on recurrence times. We used the Wald test to determine significant CpGs for recurrence. We found 1,627 CpGs with an FDR of 0.05. To investigate all combinations of the 1,627 CpGs would have required 716,490,715 individual models with 3 CpGs, hence we elected to test the 100 most significant CpG s (requiring 161,700 models) from the survival analysis to determine their predictive power for prostate cancer recurrence. We then applied the same logistic regression analysis as used for the linear regression CpGs and identified 14 more CpGs with a very strong predictive power for prostate cancer recurrence.

Logistic Regression and Receiver Operating Characteristic (ROC) curves:

After the CpGs were identified using linear regression, we used logistic regression to determine the predictive power of these CpGs for prostate cancer recurrence. Based on the sample size of 73 tumors, we elected to study all possible combinations of 3 significant CpGs along with Gleason score to determine which combinations of CpGs provided the best prediction of biochemical recurrence. We developed a logistic regression model for each of the 816 combinations of 3 CpGs and Gleason score. For each model we determined the Akaike information criterion (AIC) to determine the best predictors. We used the AIC since it judges models based on how close the fitted values tend to be to the expected values. The optimal models will minimize the AIC. We then took the models with the lowest AIC and determined the sensitivity and specificity of each model. We used the sensitivity and specificity to produce ROC curves for these models. Since a perfect predictor will have an area under the ROC curve of 1, we then calculated the area under the ROC curves and selected the model with the area closest to 1 as the best model to predict recurrence. The best model had an area of 0.97. To test the ability of the CpGs to predict recurrence we randomly selected CpGs that were not identified using linear regression. Using these CpGs we developed logistic regression models, the ROC curves, and calculated the area under these curves. For these models the area was close to 0.5, which is the expected area when a model provides no predicative power.

Identification of Diagnostic Methylation Predictive Models

A mixed model linear regression was used to identify cytosines that had differential DNA methylation measurements between patient prostate tumor tissue and patient-matched benign-adjacent tissue. Mixed model linear regression allowed us to take both individual differences and patient clinical information such as age and ethnicity into account when determining tumor-normal DNA methylation differences. We compared methylation patterns in DNA isolated from 73 patient tumor tissues and 63 benign-adjacent tissues, 52 of which were patient matched. Through this analysis, we identified 226,237 CpGs significantly differentially methylated between the tumor and benign-adjacent prostate samples.

In order to discover top potential diagnostic biomarkers from these significant CpGs, we used logistic regression on the top 100 most significant CpGs and studied all possible combinations of 3 CpGs. For each model, we calculated the Akaike Information Criterion (AIC) and Area Under the Curve (AUC), and looked for models with a minimal AIC and a maximal AUC, indicating a high predictive value. The AUC of a perfect predictive model is 1, and the top diagnostic DNA methylation model from our analysis had an AUC of 0.98.

To ensure that this predictive DNA methylation signature is robust at distinguishing prostate tumor tissue from benign-adjacent prostate tissue, we sought to validate this methylation signature in a separate cohort. We applied our top 3 CpG DNA methylation signature model in a logistic regression of Infinium HumanMethylation450 BeadChip data from The Cancer Genome Atlas (TCGA) prostate cancer project. Our diagnostic DNA methylation signature was highly accurate at distinguishing the TCGA cohort prostate tumor tissues from the benign-adjacent normal prostate tissues, and produced a ROC curve with an AUC of 0.93.

We also wanted to investigate whether this particular DNA methylation signature was prostate specific, or whether this DNA methylation pattern could distinguish tumor and normal tissues from other cancer types. To address this question, we utilized TCGA Illumina Infinium HumanMethylation450 BeadChip data collected on pancreatic, lung, and breast cancers. When applying our top statistical model from prostate cancer in these three cancer datasets, the AUC for breast cancer was 0.60, pancreatic cancer was 0.64, and lung cancer was 0.44. The predictability of our top prostate diagnostic model in pancreatic and lung cancer was not significantly different from having no predictive information (AUC of 0.5), and in breast cancer, our model proved to be only slightly better than no predictive information. Therefore, our diagnostic model is specifically predictive for prostate cancer, and is not a more general marker of tumor cells.

Additionally, we investigated potential diagnostic markers from significant CpGs that demonstrated an increase in methylation in tumors (removing those CpGs that were significant but had a decrease in DNA methylation in the tumors), as biomarkers that are hypomethylated in the tumor tissues are often difficult to detect, and thus are not as powerful in the clinic. To identify potential diagnostic biomarkers from CpGs that had more methylation in the prostate tumor tissues, we took the top 100 most significant CpGs from the linear mixed model that demonstrated an increase in DNA methylation in the prostate tumor tissues when compared to the benign-adjacent tissues. As described above, we used logistic regression to study all possible combinations of 3 CpG models. We applied the top model in our cohort, with an AUC of 0.97, to the TCGA cohort of prostate tissues, and found that it validated with an AUC of 0.92.

Identification of Additional Prognostic CpGs

In the original patent paperwork, we identified 14 CpG loci with DNA methylation levels statistically associated with biochemical recurrence using Survival Analysis. Since the initial filing, we have implemented an improved and more consistent method to calculate Area Under the Curve (AUC) using a Wilcoxon Ranked-based procedure versus empirical curve fitting techniques. We repeated analysis of the top 100 CpGs from survival analysis using our updated AUC analysis method, and ultimately identified an additional 9 CpG loci that have high predictive ability for distinguishing patients that will biochemically recur, versus patients that have not undergone biochemical recurrence.

We claim:

1. A method for determining the presence of a biochemical reoccurrence of prostate cancer in an individual in need thereof, and treating the prostate cancer, wherein in said individual has undergone previous treatment for prostate cancer, the method comprising:
    (a) determining the methylation level of at least one cytosine within a DNA region in a sample from the individual where the DNA region is at least 90% identical to SEQ ID NO: 2;
    (b) comparing the methylation level of the at least one cytosine to a threshold value for the at least one cytosine, wherein the threshold value distinguishes between individuals with and without a biochemical recurrence of prostate cancer, wherein the comparison of the methylation level to the threshold value is predictive of the presence of the biochemical reoccurrence of prostate cancer in the individual;
    (c) determining that the individual has a biochemical recurrence of prostate cancer based on the compared methylation levels in step (b); and
    (d) administering a treatment for the biochemical recurrence of prostate cancer to the individual.

2. The method of claim 1 wherein said sample is a biopsy sample.

3. The method of claim 1 wherein said sample is a blood sample.

4. The method of claim 1 wherein said sample is a urine sample.

* * * * *

SEQUENCE LISTING

```
<160> NUMBER OF SEQ ID NOS: 66

<210> SEQ ID NO 1
<211> LENGTH: 122
<212> TYPE: DNA
<213> ORGANISM: Homo sapiens

<400> SEQUENCE: 1
ggaagcagct ttccccacac gccgccttta acagcatttg gattcgcgaa gctgtgcaca      60
cgtcattttt atcgcaaaaa tgaaacctgc cggtgccgtt ttaaacagca gagttggctc     120
ag                                                                    122

<210> SEQ ID NO 2
<211> LENGTH: 122
<212> TYPE: DNA
<213> ORGANISM: Homo sapiens

<400> SEQUENCE: 2
acagcatttg gattcgcgaa gctgtgcaca cgtcattttt atcgcaaaaa tgaaacctgc      60
cggtgccgtt ttaaacagca gagttggctc agtgtccect cagtgctttc tttggctttt    120
``` tc                                                                          122

<210> SEQ ID NO 3
<211> LENGTH: 122
<212> TYPE: DNA
<213> ORGANISM: Homo sapiens

<400> SEQUENCE: 3
aggtgcctta gttactggac agagaccccg ggttccttag ttactggaca gagagtgctg      60
cgcttcaggt gccatggcct cagtttcctc ctttctgaag tgatgaaaat acattgtgcg     120
cc                                                                          122

<210> SEQ ID NO 4
<211> LENGTH: 122
<212> TYPE: DNA
<213> ORGANISM: Homo sapiens

<400> SEQUENCE: 4
tccattggaa ggtcagttgc agtgcagccc ttttccgggg taataagttt ttaatgtaga      60
cgcaattagt gaataagcag ttgattagtt cattacgaaa atagtgaaaa caacaccatt     120
tg                                                                          122

<210> SEQ ID NO 5
<211> LENGTH: 122
<212> TYPE: DNA
<213> ORGANISM: Homo sapiens

<400> SEQUENCE: 5
ctccgcggga ctcctgggcc ggcctcgccg cctctccggc ggggaacctt ccccagcccc      60
cgtccgcaca gatccctagc gccccgagcc cccgcccttc gcgcctaggc gtgcgccggc     120
tc                                                                          122

<210> SEQ ID NO 6
<211> LENGTH: 122
<212> TYPE: DNA
<213> ORGANISM: Homo sapiens

<400> SEQUENCE: 6
aagaatcttc cttttctcta gagccaagag aacaggctca aaccaaataa actagccata      60
cgatcttcta aatgccccag tgtgttcaca gtgaacacat tactttcata tgccaaaaag     120
tc                                                                          122

<210> SEQ ID NO 7
<211> LENGTH: 122
<212> TYPE: DNA
<213> ORGANISM: Homo sapiens

<400> SEQUENCE: 7
ctggagacgt gcacacgcct gggaacaggt gctgggcgg cacccaagca cgggagccag      60
cgttggggaa gcggcacacc ccagggagct agcgctggca aagcacaccc accaagagtg     120
ag                                                                          122

<210> SEQ ID NO 8
<211> LENGTH: 122
<212> TYPE: DNA
<213> ORGANISM: Homo sapiens -continued

```
<400> SEQUENCE: 8
agccaactcc tcacccgcct ggggactgct tggggcagcc catagtggga gccctggggc      60
cgctagattg aatcacttt tctatttttgg agcagccta t actcccctct gcctctggct    120
ta                                                                    122

<210> SEQ ID NO 9
<211> LENGTH: 122
<212> TYPE: DNA
<213> ORGANISM: Homo sapiens

<400> SEQUENCE: 9
ggcgtcggga agtgttcttg gtcagagcag agaaactgca gttgccttgt gctttcttcc      60
cggagagccc tgcagctgac cctctgccag agctttgggt caggctttct gactgaccct    120
ta                                                                    122

<210> SEQ ID NO 10
<211> LENGTH: 122
<212> TYPE: DNA
<213> ORGANISM: Homo sapiens

<400> SEQUENCE: 10
acagttgtga gccaccgcgc ccagccacta gttattcact ttcttgtttg aacttttgat      60
cgtttattcc tttactcggc tgcccattca tttgttaata cacttatgaa atattcaatg    120
ac                                                                    122

<210> SEQ ID NO 11
<211> LENGTH: 122
<212> TYPE: DNA
<213> ORGANISM: Homo sapiens

<400> SEQUENCE: 11
aacccatgag caaacacact cgagtctctc actgtgtaaa ttctactgtg ctgagagctg      60
cggtgaatac aaaagaaaac aactcaattc ctcaagtgtg tgccgatggc cccgtgtgg    120 tt                                                                    122

<210> SEQ ID NO 12
<211> LENGTH: 122
<212> TYPE: DNA
<213> ORGANISM: Homo sapiens

<400> SEQUENCE: 12
gttaagtctt tggactatcc ctttcctcct tgactactgc tttgacgtac ctaaatcatt      60
cgtcttacat gtcagaggaa attagttttg datagttctc ctttctgctg tacctcatgg    120
gg                                                                    122

<210> SEQ ID NO 13
<211> LENGTH: 122
<212> TYPE: DNA
<213> ORGANISM: Homo sapiens

<400> SEQUENCE: 13
gatgcccact ggataggaat tcaccaattc tcctctgagt tcatttttcta aaggatagag      60 cgacaacaca aaataccctta agtaagagaa gggaggaggg cataaggagg gtttgttccc    120
ct                                                                    122
```

<210> SEQ ID NO 14
<211> LENGTH: 122
<212> TYPE: DNA
<213> ORGANISM: Homo sapiens

<400> SEQUENCE: 14
caagtacagg gttaaatgaa ctaagtaagg catgtaaaca gcttagttta atgtttggcc        60
cgtggtatac aatctagcat tagccatcat tattggtaac ccttgtttag gcagcctttc       120
tg                                                                     122

<210> SEQ ID NO 15
<211> LENGTH: 122
<212> TYPE: DNA
<213> ORGANISM: Homo sapiens

<400> SEQUENCE: 15
ggccaggagc tggaaaggcg ctgagcccag gtggctttca ctccctgtgt gtgaggccat        60
cgctcagcat ctgcacgctg tctgctgcgt ctaacgaccc ctcctctagg ttggggatcc       120
tg                                                                     122

<210> SEQ ID NO 16
<211> LENGTH: 122
<212> TYPE: DNA
<213> ORGANISM: Homo sapiens

<400> SEQUENCE: 16
aattaaggtt ataagtaaaa tactcctcag atatttgact gaaagtatat gcttgctctt        60
cgtactttgt aggaagagca cagagaggca ggaaaggaaa ggaatgggtt ttggagagca       120
ca                                                                     122

<210> SEQ ID NO 17
<211> LENGTH: 122
<212> TYPE: DNA
<213> ORGANISM: Homo sapiens

<400> SEQUENCE: 17
gattgcagac ggagtcttgt tcactcagtg ctcaatgttg cccaggctgg agtgcagtgg        60
cgccatctcg gctagctacg acctccacct cccagccgcc tgccttggcc tcccaaagtg       120
ct                                                                     122

<210> SEQ ID NO 18
<211> LENGTH: 122
<212> TYPE: DNA
<213> ORGANISM: Homo sapiens

<400> SEQUENCE: 18
tgtccactac ctcctggcct gccacttggc tgtgagtcct ttctgggcgg tgtccagggg        60
cggttccagt gatcaggcag gtgctgagaa gcacaggcag gtgagttaag cactggaaga       120
ag                                                                     122

<210> SEQ ID NO 19
<211> LENGTH: 122
<212> TYPE: DNA
<213> ORGANISM: Homo sapiens

<400> SEQUENCE: 19
tgctgtaacg ttgacttttc aggagtggca gtagccactg gaatagagag tctcccctgc        60

```
cgttccttg gcaaatcatg ttatttcca ggctaaaact ccactttccc tagcacttgg    120
aa                                                                  122

<210> SEQ ID NO 20
<211> LENGTH: 122
<212> TYPE: DNA
<213> ORGANISM: Homo sapiens

<400> SEQUENCE: 20
aatggtggcc accctgacag cgcagtgacc agaggggat cggaggcctt ggggacaggt    60
cggaaaacgt ttgtcaggcc catagccgtg tgcacgtgat gctttgtggt gcacacttct   120
gt                                                                  122

<210> SEQ ID NO 21
<211> LENGTH: 122
<212> TYPE: DNA
<213> ORGANISM: Homo sapiens

<400> SEQUENCE: 21
tgagggtctc tcaccgagtc tctccttcag aagcacatca aggagcacca cgaggaggtc    60
cgggagcggc cctgccccca ccctggctgc aacaaggttt tcatgatcga ccgctacctg   120
ca                                                                  122

<210> SEQ ID NO 22
<211> LENGTH: 122
<212> TYPE: DNA
<213> ORGANISM: Homo sapiens

<400> SEQUENCE: 22
gcctagatgg tggccggtgt ttcctggttg cttactggtc tttctgagtt ctggttcact    60
cgcagtgaat caacttcctt tcacaagctc tgccactcac gggccattga ggaagaccct   120
tg                                                                  122

<210> SEQ ID NO 23
<211> LENGTH: 122
<212> TYPE: DNA
<213> ORGANISM: Homo sapiens

<400> SEQUENCE: 23
gtttcagaac agaaggaaga agggaaatga attcaaaggc tttcctccaa tttccagctc    60
cgtaaagcag gacaaataaa gcaaaagtaa aggcagccaa ataacatcc atttaacaag   120 ta                                                                  122

<210> SEQ ID NO 24
<211> LENGTH: 122
<212> TYPE: DNA
<213> ORGANISM: Homo sapiens

<400> SEQUENCE: 24
agcctggcat cttaatgcag ccagatgcat gaggtcccag ttactcaggc tcctgcagag    60
cgtccattga gtgatggaca atggaagtat gatggaaacg tttctctaat tgtctgaggt   120
gg                                                                  122

<210> SEQ ID NO 25
<211> LENGTH: 122
<212> TYPE: DNA
<213> ORGANISM: Homo sapiens
```

<400> SEQUENCE: 25
cgggttcaca gctcagcgct cgggacaggg cgcagcagcc gacacccgac ctgaagccga    60
cggccacgca ggtgggcaag agggtgagtt cccagctgct ggctccagcc acgggatgcg   120
cc                                                                  122

<210> SEQ ID NO 26
<211> LENGTH: 122
<212> TYPE: DNA
<213> ORGANISM: Homo sapiens

<400> SEQUENCE: 26
gttaatgaga cattagctca tttcacatcc taaatccaaa ccctcttccc ttggctaaca    60
cggggctggg ttgggatgtt cacattgacc ataatcattg ggaaaagaaa cttagggact   120
tc                                                                  122

<210> SEQ ID NO 27
<211> LENGTH: 122
<212> TYPE: DNA
<213> ORGANISM: Homo sapiens

<400> SEQUENCE: 27
aggctgagac tagggcatca aatcctaata gcctctgttt actgagcaca cagtctgtgc    60
cgtgtcctgt gctgaggact tgataggcat tatctctttt aatcctccca attcctggtg   120
gg                                                                  122

<210> SEQ ID NO 28
<211> LENGTH: 122
<212> TYPE: DNA
<213> ORGANISM: Homo sapiens

<400> SEQUENCE: 28
tcctggatgg tgggacctac cactgagccc atatgtacag ttgcagtttc cctggttccc    60
cgtggcagcc caggaaactg atgcccatcc aaaggtcatt gaccccagag gctcccaaga   120
ac                                                                  122

<210> SEQ ID NO 29
<211> LENGTH: 122
<212> TYPE: DNA
<213> ORGANISM: Homo sapiens

<400> SEQUENCE: 29
gctctccctc atttgccgtc cccttggctg tggagcagaa tctccatcga gcagttgctc    60
cgctggacaa gctcgttctg gatgggaca tgaatctacg ctactaccag gacttccgtg    120
gc                                                                  122

<210> SEQ ID NO 30
<211> LENGTH: 122
<212> TYPE: DNA
<213> ORGANISM: Homo sapiens

<400> SEQUENCE: 30
ctcaaagggt taagcaggtg cctctccggg cgaggcgcta ttggccgagg gctggggcgg    60
cgcggccgcg gtcaccacgc ttcgccgatc ccaacttggg ttcctgcgga aggcaaggcg   120
gc                                                                  122

<210> SEQ ID NO 31
<211> LENGTH: 122
<212> TYPE: DNA
<213> ORGANISM: Homo sapiens

<400> SEQUENCE: 31 ggattttag gggctcttga gctggaattt tttgggggc gccggaggt gtgctgggc        60 cgcagacccc atacaggagg taagttagag aaccacacgc aggggaggga tgctgctgct   120
tc                                                                   122

<210> SEQ ID NO 32
<211> LENGTH: 122
<212> TYPE: DNA
<213> ORGANISM: Homo sapiens

<400> SEQUENCE: 32
ccggaacacc cgtggtgacc gccgggaccc tgcctgtgac tctccaggac tctgcgaccc   60
cgggatggat attgcgatgc tggtctcgac cctgaaaccc tccctcggat ctgtgacctc   120
gg                                                                   122

<210> SEQ ID NO 33
<211> LENGTH: 122
<212> TYPE: DNA
<213> ORGANISM: Homo sapiens

<400> SEQUENCE: 33
cgcggctggg cggagacccg catctgtagg gtgcagggct gtcccggagc cttctgcccc   60
cgccctctct agccacgccg aggcatagga ggggccctgc ccggcagccc cagcccaggc   120
gg                                                                   122

<210> SEQ ID NO 34
<211> LENGTH: 122
<212> TYPE: DNA
<213> ORGANISM: Homo sapiens

<400> SEQUENCE: 34
cccacggcag gcccatcacc tgccaccagc ctaccttgca agggacagtg tggggcttgc   60
cgatcttgtt cccccagtag cctctgcgca cggggacgat ggagagcttg gccaggatga   120
tg                                                                   122

<210> SEQ ID NO 35
<211> LENGTH: 122
<212> TYPE: DNA
<213> ORGANISM: Homo sapiens

<400> SEQUENCE: 35
gtaatgagaa ggctggggac actacccctg agacctggag gagctttttt ttaactgaga   60
cgagtcctca tgctagctag ctcattccta ggtaacctgg cctctagagt cacacattaa   120
at                                                                   122

<210> SEQ ID NO 36
<211> LENGTH: 122
<212> TYPE: DNA
<213> ORGANISM: Homo sapiens

<400> SEQUENCE: 36
gcagcatggt gggcgtctac aacggcaaga ccttcaacca ggtggagatc aaggtgtgtg   60

```
cggccgtccc tgccggctgg ggtgggctgg ggtcgcctga tgcaggcggg atcagctgac    120
ac                                                                   122

<210> SEQ ID NO 37
<211> LENGTH: 122
<212> TYPE: DNA
<213> ORGANISM: Homo sapiens

<400> SEQUENCE: 37
ccatccatcc cacaagcatt ctggttcact cttgatgttt tttcactatt actaatattt    60
cgaccctgaa tatcaatctg aactatgaca gctcttagta agaaattcat tctaggtcct    120
ta                                                                   122

<210> SEQ ID NO 38
<211> LENGTH: 122
<212> TYPE: DNA
<213> ORGANISM: Homo sapiens

<400> SEQUENCE: 38
aagccagctc actttatgtc ctccaaactc accctaactt ctcgtttggg tctcatcccg    60
cggggctgct gggaaataag ctccgccacc acagtggttc ctccgccctg tgggagtggg    120
gg                                                                   122

<210> SEQ ID NO 39
<211> LENGTH: 122
<212> TYPE: DNA
<213> ORGANISM: Homo sapiens

<400> SEQUENCE: 39
tcaggctgca gaggaaacct gggggcgggg gtcgaggaag ccgagccccg aggctcccag    60
cgccgcccca ggaggaatct tgcgggccac tagaagctgt gcgcgcggcc gggctcggcc    120
cc                                                                   122

<210> SEQ ID NO 40
<211> LENGTH: 122
<212> TYPE: DNA
<213> ORGANISM: Homo sapiens

<400> SEQUENCE: 40
gcagttgctg ccacaagagt gtccagtggg cgcccaggcc acctgcggac agtttgccag    60
cgatgtccag tttgtcctga ggcgcacagg gcccagccta gctgggaggc cctcctcaga    120
ca                                                                   122

<210> SEQ ID NO 41
<211> LENGTH: 122
<212> TYPE: DNA
<213> ORGANISM: Homo sapiens

<400> SEQUENCE: 41
taggccaggc tgagcagccc aggcctggcg ggcgagcacc gttcccacat aaatcaccag    60
cgccagagtc tcgggaaaag gcgcattttt cattgctggc tgcagggcga ctccagaccg    120
cg                                                                   122

<210> SEQ ID NO 42
<211> LENGTH: 122
<212> TYPE: DNA
```

<213> ORGANISM: Homo sapiens

<400> SEQUENCE: 42

| gcggcagagg | accagcatgc | agggcgcggt | caccgtcacc | atgctgctgg | gcgtgtttac | 60 |
| cgtgtgctgg | gccccgttct | tccttcatct | cactttaatg | ctttcttgcc | ctcagaacct | 120 |
| ct | | | | | | 122 |

<210> SEQ ID NO 43
<211> LENGTH: 122
<212> TYPE: DNA
<213> ORGANISM: Homo sapiens

<400> SEQUENCE: 43

| ggtcccctga | gtctccgggt | ccaagatcga | ccccgaggct | gcgggacctg | cagagatcct | 60 |
| cgacccggga | gagccccagg | cgcctttacc | tggtttcatc | ttcagttgag | gccaaaatct | 120 |
| cc | | | | | | 122 |

<210> SEQ ID NO 44
<211> LENGTH: 122
<212> TYPE: DNA
<213> ORGANISM: Homo sapiens

<400> SEQUENCE: 44

| gggggactcc | catggagcgc | ggactcctaa | ggaagtcgct | gggaatccca | ccggctgtac | 60 |
| cgcagggcgt | tagtacctag | atggcttcgg | tgcccccaag | cgatgggctc | aagctacagg | 120 |
| gc | | | | | | 122 |

<210> SEQ ID NO 45
<211> LENGTH: 122
<212> TYPE: DNA
<213> ORGANISM: Homo sapiens

<400> SEQUENCE: 45

| ggcggcgccg | ggggccccgg | ggtctcgacc | cgaataaggc | ggtgtggggg | agagccgtgg | 60 |
| cgcggggcg | gcgtgggtcc | ggggcgaca | ggggtggcga | gggcggcgga | gccggacgac | 120 |
| cc | | | | | | 122 |

<210> SEQ ID NO 46
<211> LENGTH: 122
<212> TYPE: DNA
<213> ORGANISM: Homo sapiens

<400> SEQUENCE: 46

| cttgctgggg | aaattgctgt | ttttgatctt | ttaatccttt | ctccctgcac | ctcacccttc | 60 |
| cgtcttacca | aggaggaaat | gaggctccag | ggatgagggc | cttatcttgg | actttatggg | 120 |
| tg | | | | | | 122 |

<210> SEQ ID NO 47
<211> LENGTH: 122
<212> TYPE: DNA
<213> ORGANISM: Homo sapiens

<400> SEQUENCE: 47

| ttaatccatc | acaatgagac | gttctattct | gggcaggcgg | cgcgagcaga | tgctgggcgc | 60 |
| cggcggaggc | agcgtgcagg | gctggcgctc | acgcaggccg | ccagcaccct | gcgctccacc | 120 |
| cc | | | | | | 122 |

<210> SEQ ID NO 48
<211> LENGTH: 122
<212> TYPE: DNA
<213> ORGANISM: Homo sapiens

<400> SEQUENCE: 48
gcggcgggcc gttggggagg gtgttgggat gaggagcccc aaccagatgg acgcgcaccc    60
cgcagcggcg gaggcggcgg cgaggcttga gcagtgagtg ctcgggagcc ccggccagcc   120
ct                                                                 122

<210> SEQ ID NO 49
<211> LENGTH: 122
<212> TYPE: DNA
<213> ORGANISM: Homo sapiens

<400> SEQUENCE: 49
gtgcctttcc caactagaga attaactctt gcggggcaca aaacagcctc tatttctttg    60
cgtccccagc gcctgtttgt tgaagactga gttgaaggag tagcaggtgg tgttaatttg   120
tc                                                                 122

<210> SEQ ID NO 50
<211> LENGTH: 122
<212> TYPE: DNA
<213> ORGANISM: Homo sapiens

<400> SEQUENCE: 50
tttcgtggac tcccactgtg gaaacctgct ggtgttttgc tgcggtttca tttccctctg    60
cggaggagcc agggcaacct tggccagaca ggcacctagc tgtgcccttc tttccagggc   120
ct                                                                 122

<210> SEQ ID NO 51
<211> LENGTH: 122
<212> TYPE: DNA
<213> ORGANISM: Homo sapiens

<400> SEQUENCE: 51
gtcctaagca ctttgcaggt aaatacgtgt aatcctcaca gcaacactgg gagaaatacc    60
cgtctcacag ctgaagaaac gaagacgcag aaagggtaga cagaagtaat tttctaatta   120
cg                                                                 122

<210> SEQ ID NO 52
<211> LENGTH: 122
<212> TYPE: DNA
<213> ORGANISM: Homo sapiens

<400> SEQUENCE: 52 gaaagggggcc tgctgtggga cctgatggtg tctcccttgt caccttgtaa gcctggccct    60
cgtggccttt gtgatgcagc tccccacaga gccctccagc cttgggtcct gctgctccca   120
ca                                                                 122

<210> SEQ ID NO 53
<211> LENGTH: 122
<212> TYPE: DNA
<213> ORGANISM: Homo sapiens

<400> SEQUENCE: 53

-continued

| | |
|---|---|
| tcacatccctt tacctgctat ggctgtcagt gataccatag actcagggg tactagtctc | 60 |
| cgtaattttg tggaccatgc aaagaatgag gaaagctgta ttgagattcc tttgatgacc | 120 |
| cc | 122 |

<210> SEQ ID NO 54
<211> LENGTH: 122
<212> TYPE: DNA
<213> ORGANISM: Homo sapiens

<400> SEQUENCE: 54

| | |
|---|---|
| ccaactagag aattaactct tgcggggcac aaaacagcct ctatttcttt gcgtccccag | 60 |
| cgcctgtttg ttgaagactg agttgaagga gtagcaggtg gtgttaattt gtcaaaaga | 120 |
| tg | 122 |

<210> SEQ ID NO 55
<211> LENGTH: 122
<212> TYPE: DNA
<213> ORGANISM: Homo sapiens

<400> SEQUENCE: 55

| | |
|---|---|
| ggggaggcct caggaatctt agaattgtgg cagaagagga agcaaatacg tctttcttca | 60 |
| cgtggcagca ggaaggagaa gtgccgagtg aatggggaaa agccccttat aaaaccatca | 120 |
| ga | 122 |

<210> SEQ ID NO 56
<211> LENGTH: 122
<212> TYPE: DNA
<213> ORGANISM: Homo sapiens

<400> SEQUENCE: 56

| | |
|---|---|
| acaggtacag gagctgtgcc actgaactct acggaggtat agtgtctgga agctcaggta | 60 |
| cggggcggcc agacacacac aaagctgtag tgtgattttc cctgcaggat atctcggcct | 120 |
| ag | 122 |

<210> SEQ ID NO 57
<211> LENGTH: 122
<212> TYPE: DNA
<213> ORGANISM: Homo sapiens

<400> SEQUENCE: 57

| | |
|---|---|
| tctcaccacc tgccccgagc ctcgcttcgc caaaggagca ctgggtcctg cgcaacagct | 60 |
| cggaggcgct ggggtcctaa gttcctggcc ccacggcgca cagcttcccc accgcacagc | 120 |
| cc | 122 |

<210> SEQ ID NO 58
<211> LENGTH: 122
<212> TYPE: DNA
<213> ORGANISM: Homo sapiens

<400> SEQUENCE: 58

| | |
|---|---|
| ctgcaagatc gtggtggtgg gagacgcaga gtgcggcaag acggcgctgc tgcaggtgtt | 60 |
| cgccaaggac gcctatcccg gggtgaggga cctgcgtctt ggaggggga cgctaaggct | 120 |
| gc | 122 |

<210> SEQ ID NO 59
<211> LENGTH: 122

```
<212> TYPE: DNA
<213> ORGANISM: Homo sapiens

<400> SEQUENCE: 59
cccacggcgc acagcttccc caccgcacag cccccagcgt acagggcccc tgccggccgc    60
cgcctgccca ccctgcttgc cgcccaccgg tccccgctcg ccccatctc agcctcatct    120 ct                                                                  122

<210> SEQ ID NO 60
<211> LENGTH: 122
<212> TYPE: DNA
<213> ORGANISM: Homo sapiens

<400> SEQUENCE: 60
ggcgaggaga tgaaggggtc gtcttcatct tcgccggatg atttccgccc acatagaggg    60
cgccagtgac gcccacacac gtgctggtgt cccgggaaga gttcctggca aagagctcag    120
ga                                                                  122

<210> SEQ ID NO 61
<211> LENGTH: 122
<212> TYPE: DNA
<213> ORGANISM: Homo sapiens

<400> SEQUENCE: 61
gcaaagcgca aaggcccggg cgccggccct gccgccgccg ccagttcatt ttcatagagt    60
cgcccgagct taacgtcgcc ttgcacgtgt tttctaagct ccacaggtgg ctttggggta    120
ca                                                                  122

<210> SEQ ID NO 62
<211> LENGTH: 122
<212> TYPE: DNA
<213> ORGANISM: Homo sapiens

<400> SEQUENCE: 62
tgcggaccct gctccgctac tacaaccaga gcgaggcggg tgagtgaccc cggcccgggg    60
cgcagatcac ttactccccg ctccatgcct cacggacggc cctggtcccc tgagtctccg    120
gg                                                                  122

<210> SEQ ID NO 63
<211> LENGTH: 122
<212> TYPE: DNA
<213> ORGANISM: Homo sapiens

<400> SEQUENCE: 63
gaggcgggtg agtgaccccg gcccggggcg cagatcactt actccccgct ccatgcctca    60
cggacggccc tggtcccctg agtctccggg tccaagatcg accccgaggc tgcgggacct    120
gc                                                                  122

<210> SEQ ID NO 64
<211> LENGTH: 122
<212> TYPE: DNA
<213> ORGANISM: Homo sapiens

<400> SEQUENCE: 64
cagctggtgg gggcgccgca ggttagagac gtgaggccgc gaggctgagg gctgtgaagg    60
cggtgggcac gcacggcgtg ccggggccgc ctggcttcgc ggcggggag gtaacactgc    120
```

```
ga                                                                          122

<210> SEQ ID NO 65
<211> LENGTH: 122
<212> TYPE: DNA
<213> ORGANISM: Homo sapiens

<400> SEQUENCE: 65
ctcaccagcc cgggaaggca agccccagtc aggcggaagg tagctggctg cggggcgggg           60
cgactggcgg gcggcgggag gcgccaaccg ccacagacga ctcccagctg gccgagggcg          120
gg                                                                         122

<210> SEQ ID NO 66
<211> LENGTH: 122
<212> TYPE: DNA
<213> ORGANISM: Homo sapiens

<400> SEQUENCE: 66
gggaaggcaa gccccagtca ggcggaaggt agctggctgc ggggcggggc gactggcggg           60
cggcgggagg cgccaaccgc cacagacgac tcccagctgg ccgagggcgg gaaggggca          120 gg                                                                         122
```